US007942524B2

(12) United States Patent
Smith et al.

(10) Patent No.: US 7,942,524 B2
(45) Date of Patent: May 17, 2011

(54) EYEWEAR SYSTEM FOR THE TREATMENT OF UNILATERAL NEGLECT SYNDROME

(75) Inventors: Brian Patrick Smith, Union City, GA (US); Ashanti R. Young, Birmingham, AL (US)

(73) Assignee: SY Patents LLC, Forestdale, AL (US)

(*) Notice: Subject to any disclaimer, the term of this patent is extended or adjusted under 35 U.S.C. 154(b) by 197 days.

(21) Appl. No.: 12/355,755

(22) Filed: Jan. 16, 2009

(65) Prior Publication Data

US 2010/0182564 A1 Jul. 22, 2010

(51) Int. Cl.

| | |
|---|---|
| ***A61B 3/00*** | (2006.01) |
| ***G02C 5/00*** | (2006.01) |
| ***G02C 1/02*** | (2006.01) |
| ***G02C 5/14*** | (2006.01) |

(52) U.S. Cl. ........... 351/203; 351/41; 351/110; 351/111

(58) Field of Classification Search .............. 351/41–46, 351/200–246, 110, 111, 124; 607/81–88
See application file for complete search history.

(56) References Cited

U.S. PATENT DOCUMENTS

| | | | | |
|---|---|---|---|---|
| 3,505,679 | A | 4/1970 | Bennett | 351/47 |
| 5,372,504 | A * | 12/1994 | Buechler | 434/35 |
| 5,503,637 | A | 4/1996 | Kyricos et al. | 607/88 |
| 5,745,210 | A * | 4/1998 | Biernat et al. | 351/41 |
| 6,145,983 | A * | 11/2000 | Schiffer | 351/46 |
| 6,350,275 | B1 * | 2/2002 | Vreman et al. | 607/88 |
| 6,942,336 | B2 | 9/2005 | Foulke et al. | 351/46 |
| 7,364,583 | B2 | 4/2008 | Rose | 607/88 |
| 2003/0109906 | A1 | 6/2003 | Streeter | 607/88 |
| 2006/0136018 | A1 * | 6/2006 | Lack et al. | 607/88 |
| 2006/0224217 | A1 | 10/2006 | Burgmann et al. | 607/88 |
| 2009/0237611 | A1 * | 9/2009 | Walsh et al. | 351/158 |

* cited by examiner

*Primary Examiner* — Mohammed Hasan
(74) *Attorney, Agent, or Firm* — George R. Reardon

(57) ABSTRACT

An eyewear system for the treatment of unilateral neglect syndrome is disclosed. The eyewear system is comprised of an eyewear device, a lens system, flashcards, an LED system integrated into the eyewear device, a remote control for selective activation of the LED system, and instructional media on the use of the eyewear system.

16 Claims, 28 Drawing Sheets

EYEWEAR SYSTEM FOR THE TREATMENT OF UNILATERAL NEGLECT SYNDROME

FIELD OF THE INVENTION

The technology described herein relates generally to the field of treatment systems. More specifically, this technology relates to a system for the treatment of unilateral neglect syndrome (UNS).

BACKGROUND OF THE INVENTION

The technology described herein relates to devices, and methods thereof, that aid in the rehabilitation of individuals who exhibit signs and/or symptoms of unilateral neglect as a resultant of brain dysfunction, e.g., from cerebral vascular accident, traumatic brain injury, and/or brain tumor.

Individuals with this syndrome act as though whole regions of space contralateral to their lesions do not exist. In early stages, patients may deny ownership of their contra-lateral limb and also neglect parts of their own body. When dressing, they might not clothe the contralateral side and may fail to groom their hair or shave parts of their faces on that side.

Right hemisphere damage is a more common and more severe cause of unilateral neglect than left hemisphere damage. Damage causing left-sided neglect is usually centered on the inferior parietal lobule or superior temporal lobe of the right hemisphere. Patients with such damage ignore events occurring on the left side of space. Patients may even fail to eat the food on the left side of their plate or bump into obstacles on their left side.

Individuals suffering from unilateral neglect often exhibit poor self care skills and often require 24 hour care due to poor safety awareness, secondary to inability to process/scan their entire environment. To regain as much functional independence as possible, the brain much first recognize that the neglected side of the body still exists.

Extensive assistance from external caregivers is needed in order to rehabilitate individuals with brain injuries that result in unilateral neglect symptoms and who are currently unable to perform basic activities of daily living (ADL) skills. There is a need in this field for an improved rehabilitation system that is cost effective, easy to use, and effective.

Related patents known in the art include the following: U.S. Pat. No. 3,505,679, issued to Bennett on Apr. 14, 1970, discloses a removable eye side shield.

U.S. Pat. No. 5,503,637, issued to Kyricos et al. on Apr. 2, 1996, discloses an apparatus for producing and delivering high-intensity light to the eyes of a subject to modify the subject's circadian phase. The apparatus includes a support for positioning the apparatus above the eyes of the subject, a light generator for producing a cool, high-intensity light which is radiated to the eyes of the subject, and a power source coupled to the apparatus for supplying power to the light generator. The support of the invention is preferably a visor which does not obstruct the subject's vision when positioned on the head.

U.S. Pat. No. 6,350,275, issued to Vreman et al. on Feb. 26, 2002, discloses a device for treating a circadian rhythm disorder in a subject. The device includes a plurality of light emitting diodes (LED's), preferably blue to green; a mounting to which the LED's are connected: a material for positioning the LED's within 3 cm of the subject, with an orientation toward the subject; a portable power supply electrically connected to the LED's; and a control connected to the LED's for altering the operation of the LED's. The device is sufficiently light and compact to be comfortably worn by the subject. One or more such devices are used to deliver light to a subject's retinas, to the subject's vascular tissue, or simultaneously to both the retinas and the vascular tissue. For illumination of the retina, small chip-type LED's are integrated into the frames of eyeglasses and positioned to direct light into the eyes of the subject. For illumination of the vascular tissue, an array of lens or chip type LED's are contained in a casing that is secured against the skin of the subject. The devices can be used independently of each other, or can be used in combination for more effective and/or flexible treatment.

U.S. Pat. No. 6,942,336, issued Foulke et al. on Sep. 13, 2005, discloses opaque films adhering electrostatically to lenses of eyewear to train baseball fielders and golfers. For baseball, films placed on the lower parts of the lenses encourage the player to follow a ball visually throughout its entire path of travel toward the player's glove. For golf an opaque film covers one lens, and an opaque film having a lenticular transparent opening in its upper part is placed on the other lens. The films encourage the golfer to keep the head down and behind the ball during the downswing.

U.S. Pat. No. 7,364,583, issued to Eels et al. on Apr. 8, 2008, discloses a system for exposure of eyes of a user to light. That system comprises: a head mountable housing and at least one array of light emitting diodes disposed within the housing proximate to the eyes, and whereby light emissions are transmitted to the eyes. A controller is coupled to the light emitting diodes, and controls the intensity, duration, and sequences of the light emissions. Also provided is portable electrical charge storage cell, disposed within the housing, whereby an electrical current is supplied to the at least one array of light emitting devices.

U.S. Published Patent Application 2003/0109906, inventor Streeter, published on Jun. 12, 2003, discloses therapeutic methods for the treatment of stroke; the methods including delivering a neuroprotective effective amount of light energy having a wavelength in the visible to near-infrared wavelength range to that area of the brain containing the area of primary infarct. The neuroprotective effective amount of light energy is a predetermined power density at the level of the brain tissue being treated, and is delivered by determining a surface power density of the light energy that is sufficient to deliver the predetermined power density of light energy to the brain tissue.

U.S. Published Patent Application 2006/0224217, inventor Burgmannet al., published on Oct. 5, 2006, discloses a phototherapy device which includes a light source for emitting light of a suitable wavelength and a programmable controller connectable to the light source for controlling the power supplied to the light source. A programming key is associated with the programmable controller for programming the programmable controller to control the power supplied to the light source during use. The controller is programmable to control the operating configurations only when the programming key is in communication with the controller.

U.S. Published Patent Application 2006/0136018, inventor Lack et al, published Jun. 22, 2006, discloses an apparatus for administering light to effect re-timing of the human body clock. In one form, the apparatus includes two pairs of light emitting diodes 400 having an emission wavelength in the range 450 nm to 530 nm and a frame adapted to be worn on the face of a wearer. The frame is arranged to support the two pairs of light emitting diodes 400 so that one pair of the light emitting diodes is supported adjacent a surface of each eye of the wearer. The light emitting diodes of each pair project a light output that illuminates a different area of the retina of a respective eye and are spaced apart so as to provide a viewing zone therebetween.

The foregoing patent and other information reflect the state of the art of which the inventor is aware and are tendered with a view toward discharging the inventors' acknowledged duty of candor in disclosing information that may be pertinent to the patentability of the technology described herein. It is respectfully stipulated, however, that the foregoing patent and other information do not teach or render obvious, singly or when considered in combination, the inventors claimed invention.

BRIEF SUMMARY OF THE INVENTION

In various exemplary embodiments, the technology described herein provides a system for the treatment of unilateral neglect syndrome. This system is comprised of devices and associated methods directed to the treatment of UNS.

The technology described herein utilizes one or more devices that are specifically designed to retrain the injured cerebrum of the brain to process visual stimuli to the affected side of the body so that an affected individual can regain functional scanning and tracking abilities so that he/she can actively participate in basic ADL tasks To assist an individual with unilateral neglect/inattention deficits, an eyewear system is used that gradually progresses an individual with UNS to independently scan and track objects on the affected side of the body by using lights, e.g., LED lights, and flash cards as measurable, quantifiable data to track and document progress.

The technology described herein pertains to a non-invasive retraining tool that reeducates a user to the use of the neglected side of the body. This neglect is observed in stroke or accident victims who have fairly extensive damage to the posterior (parietal or parieto-occipital) regions of the right hemisphere of the brain. It sometimes occurs after similar damage to the left hemisphere, but much less frequently and in milder form. The impression a caregiver gets in observing such a patient is that he/she behaves as if the whole left or right side of space, and sometimes even the left or right side of his/her own body, does not exist.

An advantage of the technology described herein is that benefiting from the use of these system are individuals who exhibit neglect or inattention to either the left or right side of the body and cannot complete basic activities of daily living skills due to CVA or brain injury. (Examples given include; reading, writing, upper body dressing, lower body dressing, toileting, self feeding, wheelchair propulsion, facial makeup application, shaving, brushing teeth, combing hair, cleaning dentures, donning and doffing of hearing aides, washing of hair, performing functional transfers, and tracking/scanning towards visual or auditory stimuli.)

The technology described herein provides an eyewear system to rehabilitate individuals with various brain injuries who have acquired unilateral neglect symptoms, who are currently unable to perform basic activities of daily living skills and who require extensive assistance from external caregivers.

One element of the eyewear system is an eyewear device having a frame having a front left rim area with a front left lens area, a front right rim area with a front right lens area. In some embodiments the eyewear frame is further comprised of a right side lens area and a left side lens area. Each lens area may contain a fixed clear lens, a fixed occluded lens or may be vacant.

In one embodiment, the eyewear system is comprised of a plurality of eyewear devices, each with a different configuration of fixed occluded lenses. The medical professional would select the appropriate eyewear device as appropriate. Each eyewear device can have an identifying characteristic, e.g. a number, a letter, a word, a phrase, a color, and the like, or combinations thereof.

In another embodiment, the eyewear system is comprised of a single eyewear device, having fixed clear lenses in each lens area. The eyewear system for this embodiment is further comprised of shaped thin films that are removeably attached to designated clear lenses as desired by the medical professional.

In yet another embodiment, the eyewear system is comprised of a single eyewear device, where its eyewear frame has vacant lens areas and is configured for removable attachment of plastic occluded lenses as desired by the medical professional, e.g. via a male-female attachment arrangement.

The eyewear system is further comprised by flash cards.

The eyewear system is further comprised by sensor, e.g. an infrared sensor, connected to an LED light system that is integrated into the eyewear frame.

The eyewear system is further comprised by a remote control for selective activation of the LED light system.

The eyewear system is further comprised of a plurality of thin films dimensioned for placing on at least one of the remote control buttons as desired by the medical professional.

In some embodiments the remote control is a wireless remote control.

The eyewear system is further comprised of instructional media for instructing a medical professional or a caregiver in the use of the eyewear system elements.

In one exemplary embodiment, the technology described herein provides an eyewear device. The device includes eyewear frames comprising a left rim having a left lens area for receiving a first and a second left lens, the first and second left lenses configured for placement in the left lens area individually or in combination, adjacent one to another; a right rim having a right lens area for receiving a first and a second right lens, the first and second right lenses configured for placement in the right lens area individually or in combination, adjacent one to another; where the eyewear frames are configured for disposition upon a subject, and a left eye and a right eye are partially or fully occluded in a plurality of varied patterns, to aid in the treatment of unilateral neglect syndrome and stimulate response in a neglected side of the body of the subject.

In another exemplary embodiment, the technology described herein provides an eyewear system comprising a first pair of eyewear frames having a left rim having a left lens area for receiving a first and a second left lens, the first and second left lenses configured for placement in the left lens area individually or in combination, adjacent one to another, a right rim having a right lens area for receiving a first and a second right lens, the first and second right lenses configured for placement in the right lens area individually or in combination, adjacent one to another, a left end piece hingedly attached to the left rim and having a left temple area, a right end piece hingedly attached to the right rim and having a right temple area, a removable left temple block, configured for placement within the left temple area, and a removable right temple block, configured for placement within the right temple area; a second pair of eyewear frames having all elements of the first pair of eyewear frames and additionally having a plurality of light-emitting diodes (LEDs) disposed upon the second pair eyewear frames on an inside of the left and right rims and configured to emit a plurality of varied light patterns toward the subject to provide stimulation; where the first and second pairs of eyewear frames are configured for interchangeable disposition upon a subject, and a left eye and a right eye are partially or fully occluded in a plurality of varied patterns, to aid in the treatment of unilateral neglect syndrome and stimulate response in a neglected side of the body of the subject.

In yet another exemplary embodiment, the technology described herein provides a method for treating unilateral neglect syndrome experienced by a subject comprising utilizing a first pair of eyewear frames having a left rim having a left lens area for receiving a first and a second left lens, the first and second left lenses configured for placement in the left lens area individually or in combination, adjacent one to another, a right rim having a right lens area for receiving a first and a second right lens, the first and second right lenses configured for placement in the right lens area individually or in combination, adjacent one to another, and wherein the eyewear frames are configured for disposition upon a subject, and a left eye and a right eye are partially or fully occluded in a plurality of varied patterns, to aid in the treatment of unilateral neglect syndrome; and directing the subject to wear the first pair of eyewear frames upon diagnosis of a cerebral vascular accident by a medical professional, and where the left lens area for receiving a first and a second left lens and the right lens area for receiving a first and a second right lens are partially occluded on a side of each eye corresponding to the side of the subject that is not suffering unilateral neglect.

There has thus been outlined, rather broadly, the more important features of the technology in order that the detailed description thereof that follows may be better understood, and in order that the present contribution to the art may be better appreciated. There are additional features of the technology that will be described hereinafter and which will form the subject matter of the claims appended hereto. In this respect, before explaining at least one embodiment of the technology in detail, it is to be understood that the invention is not limited in its application to the details of construction and to the arrangements of the components set forth in the following description or illustrated in the drawings. The technology described herein is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the technology described herein. It is important, therefore, that the claims be regarded as including such equivalent constructions insofar as they do not depart from the spirit and scope of the technology described herein.

Further objects and advantages of the technology described herein will be apparent from the following detailed description of a presently preferred embodiment which is illustrated schematically in the accompanying drawings.

BRIEF DESCRIPTION OF THE DRAWINGS

The technology described herein is illustrated with reference to the various drawings, in which like reference numbers denote like device components and/or method steps, respectively, and in which.

DETAILED DESCRIPTION OF THE INVENTION

Before describing the disclosed embodiments of this technology in detail, it is to be understood that the technology is not limited in its application to the details of the particular arrangement shown here since the technology described is capable of other embodiments. Also, the terminology used herein is for the purpose of description and not of limitation.

In various exemplary embodiments, the technology described herein provides an eyewear system having devices and associated methods. The eyewear system provides a caregiver with tools for the treatment of UNS. In the illustrative embodiment, the eyewear system is utilized in a medical professional environment. It will be apparent however to those in the art that the eyewear system can be utilized in varied other environments.

Figure 1:
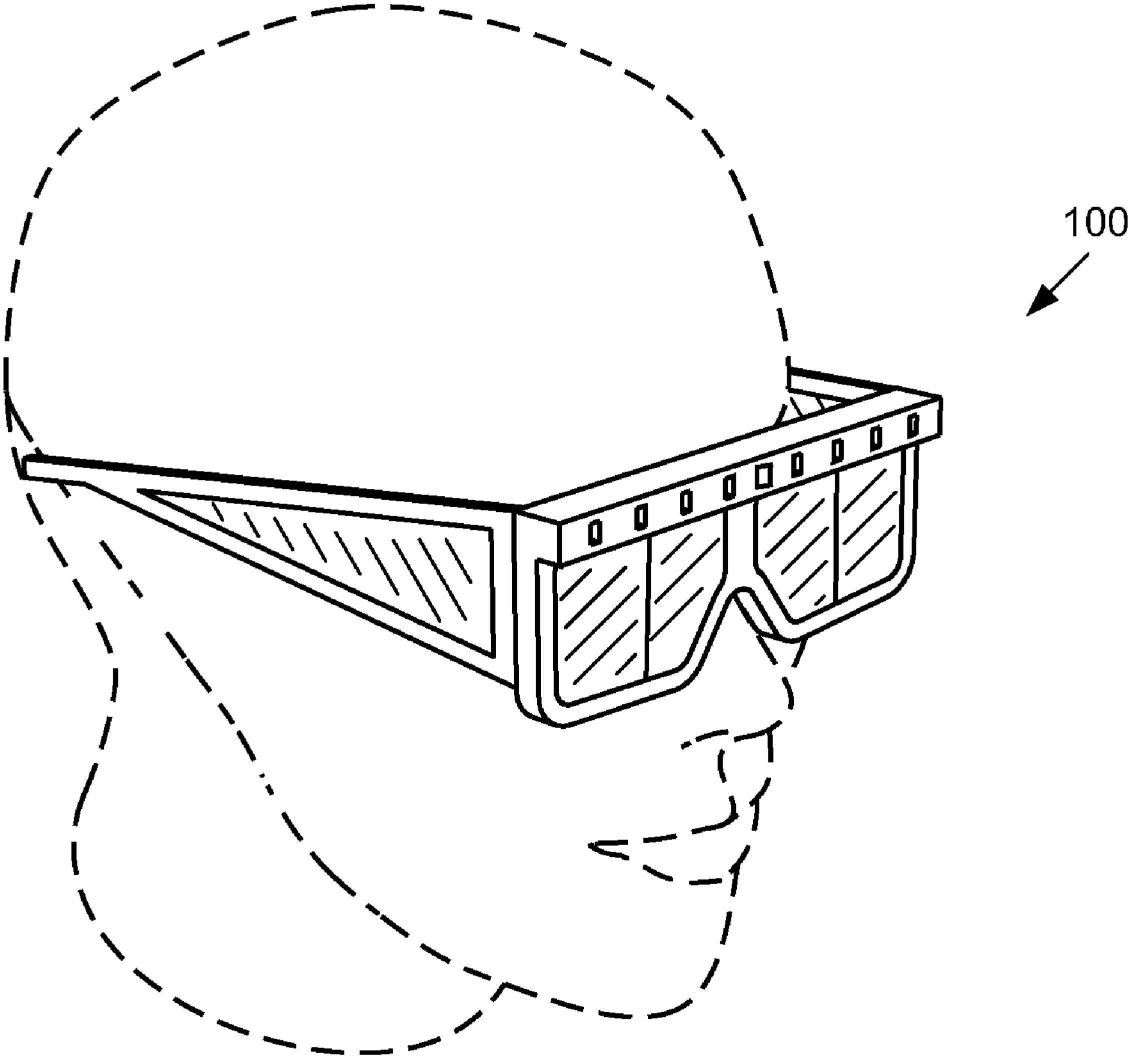
FIG. 1 is a perspective view of a patient, illustrating, in particular, an individual wearing an eyewear device, according to an embodiment of the technology described herein.
Figure 2:
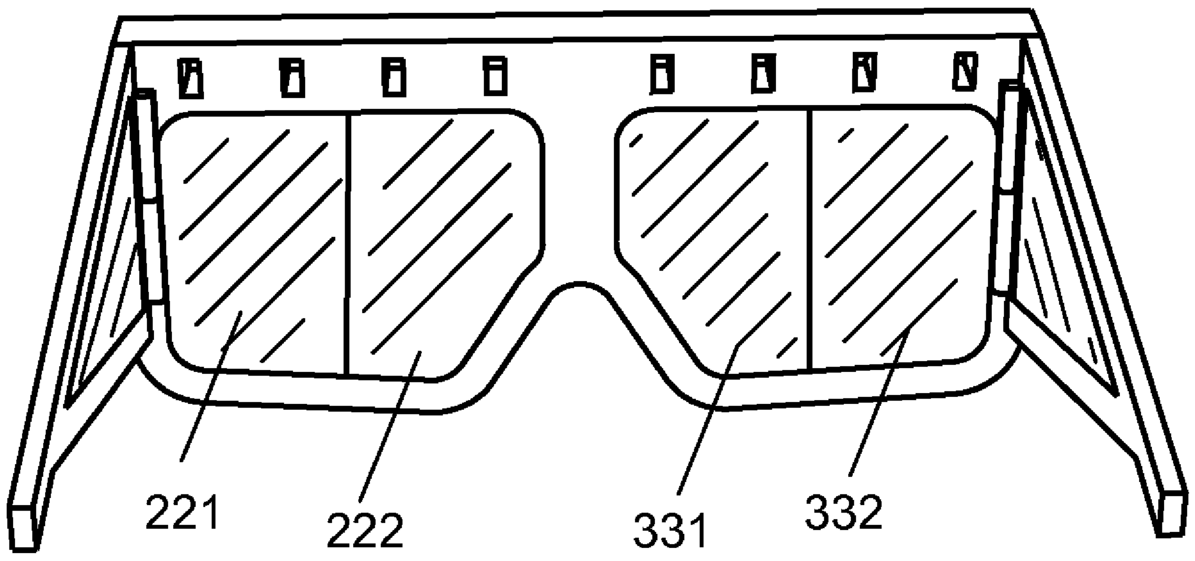
FIG. 2 is a rear view of an eyewear device, according to an embodiment of the technology described herein.
Figure 3:
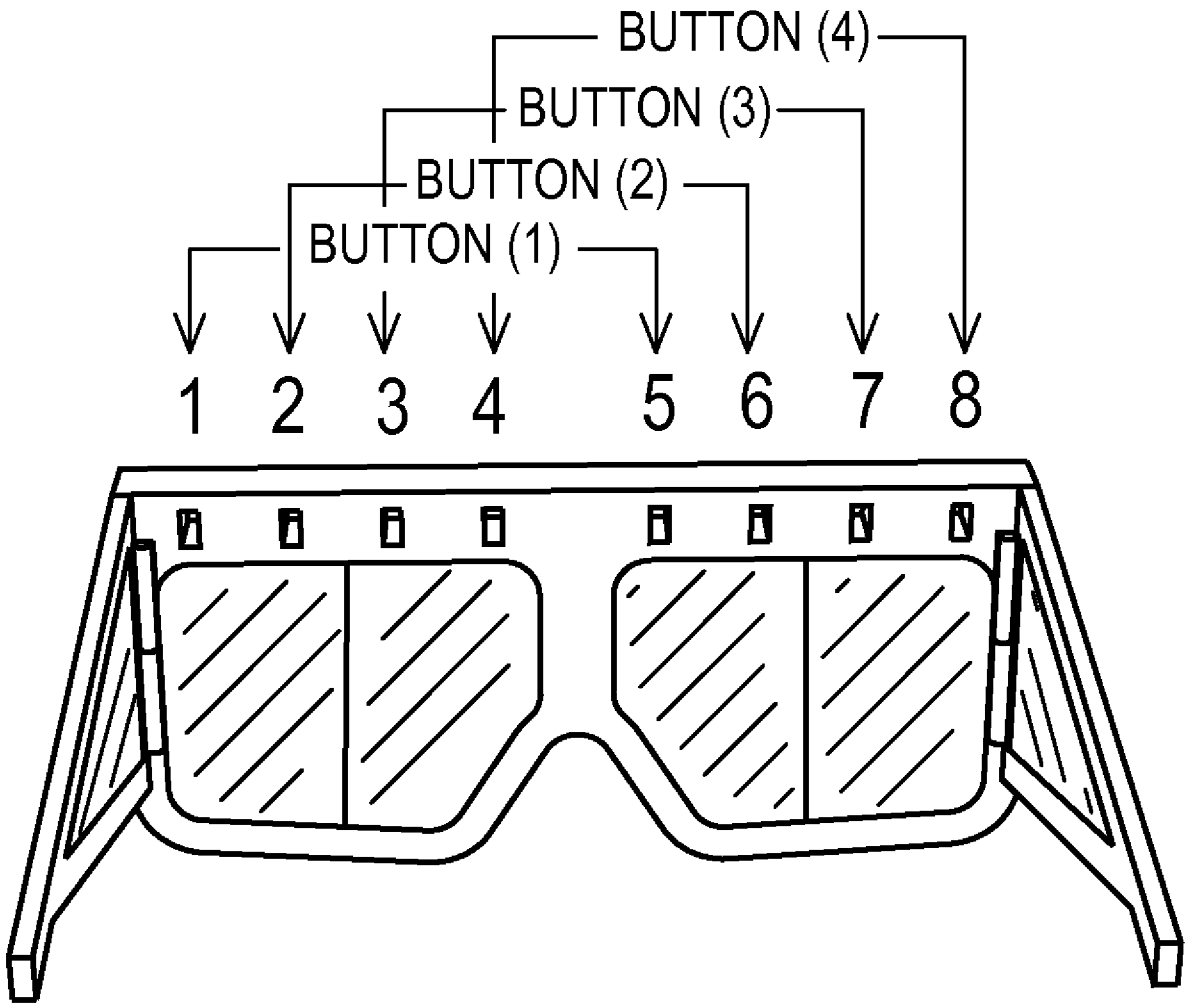
FIG. 3 is a rear view of the eyewear device of FIG. 2, illustrating, in particular, a numbering arrangement for LED lights, according to an embodiment of the technology described herein.
Figure 4:
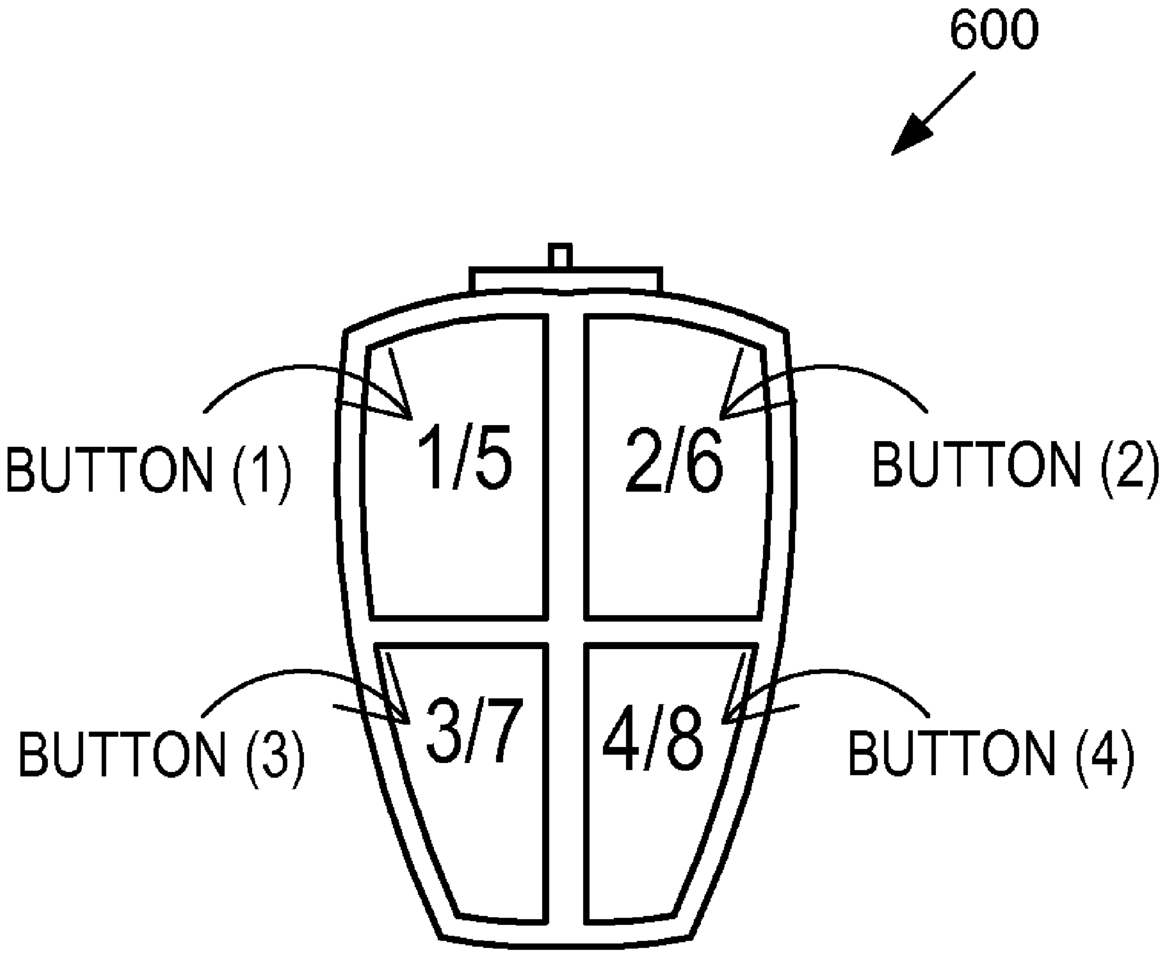
FIG. 4 is a top plan view of a remote control device, illustrating, in particular, button arrangements corresponding to LED lights for the eyewear device of FIG. 3, according to an embodiment of the technology described herein.
Figure 5:
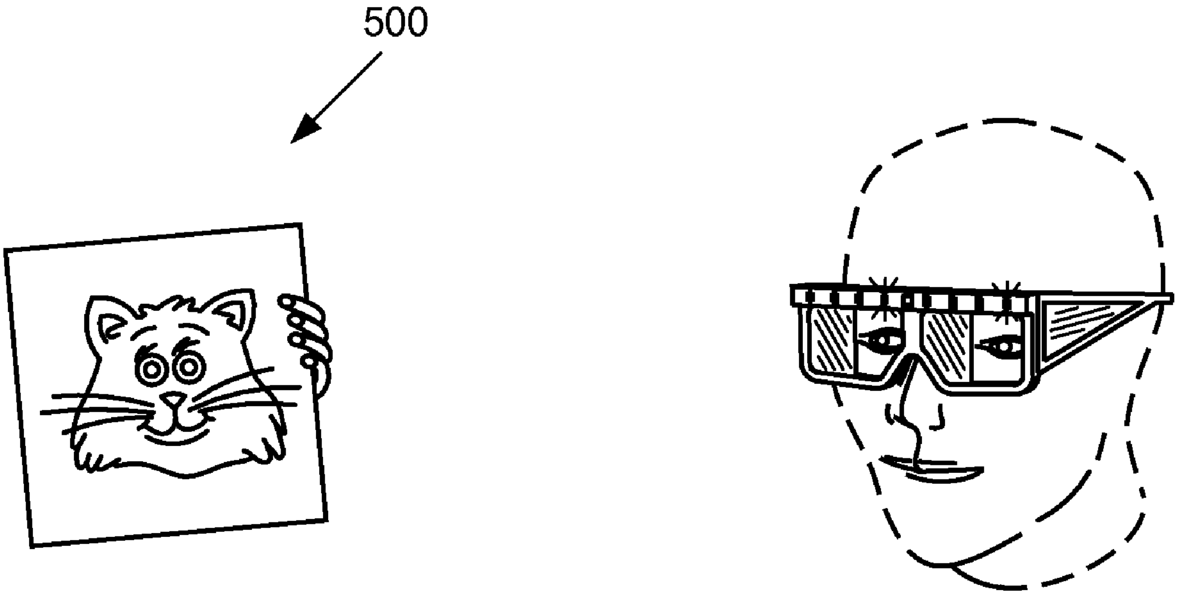
FIG. 5 illustrates the use of a flashcard with an individual wearing an eyewear device having partially occluded lenses installed, according to an embodiment of the technology described herein.
Figure 6:
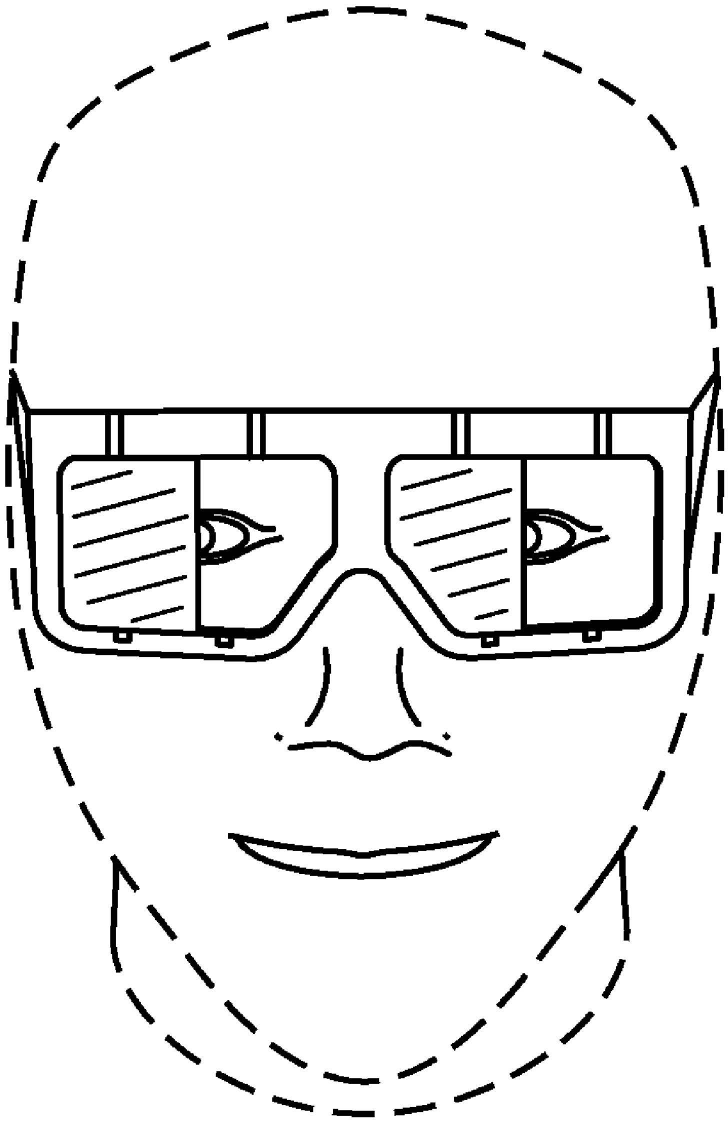
FIG. 6 illustrates an individual wearing an eyewear device, illustrating, in particular, partially occluded lenses installed, according to an embodiment of the technology described herein.
Figure 7:
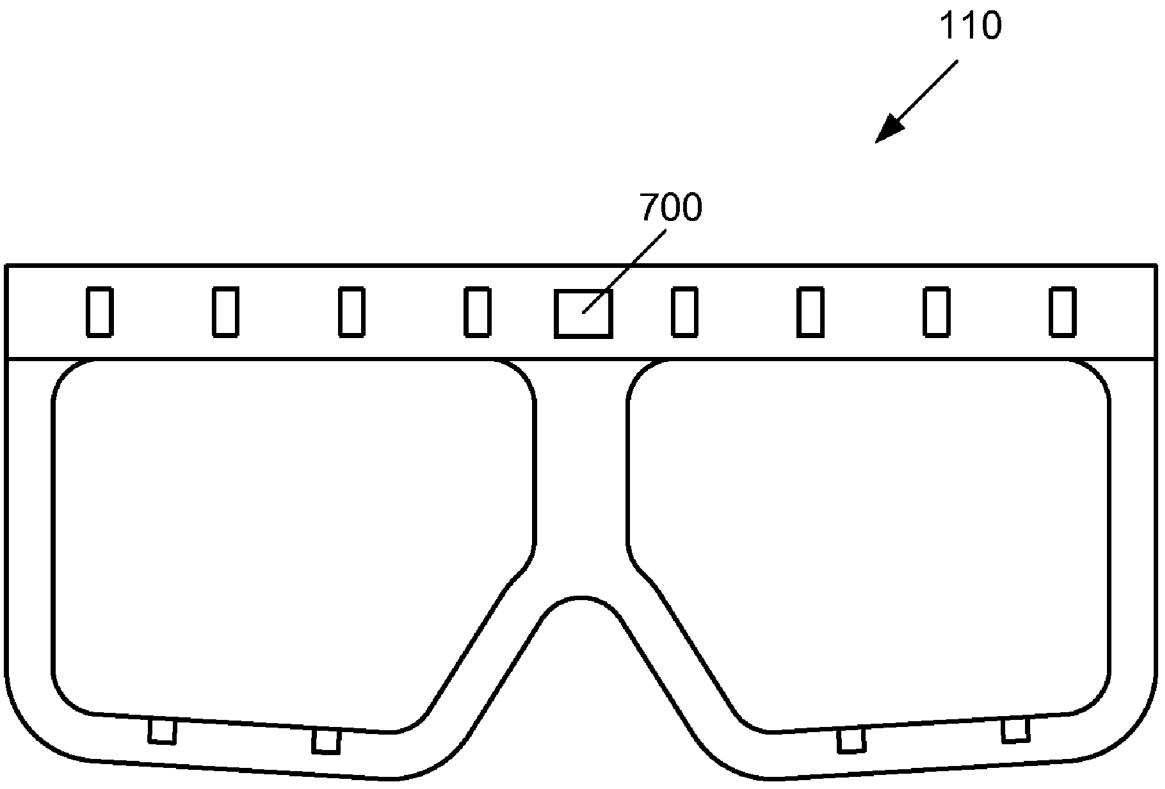
FIG. 7 is a front plan view of an eyewear device, according to an embodiment of the technology described herein.
Figure 8:
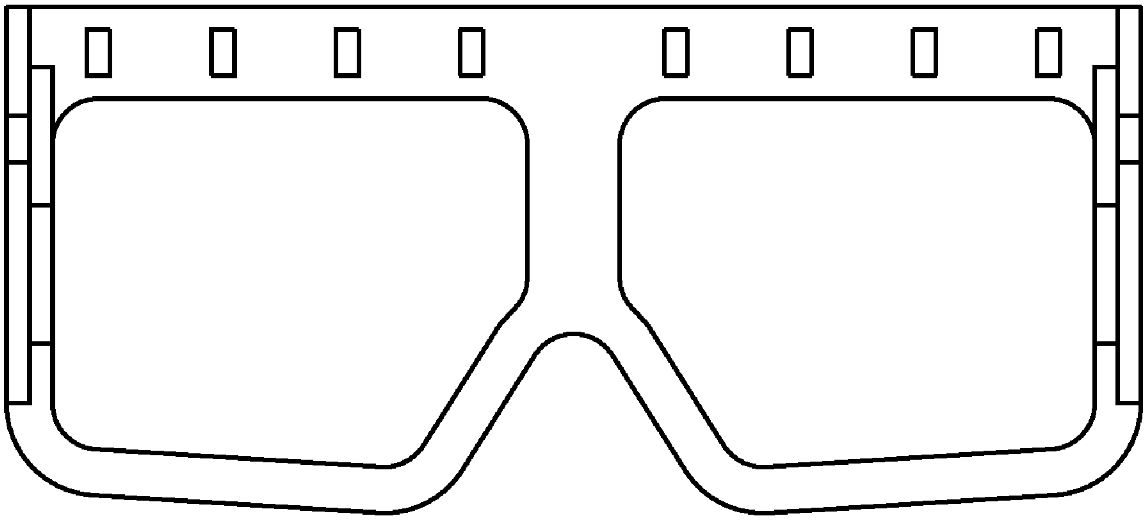
FIG. 8 is a rear plan view of an eyewear device, according to an embodiment of the technology described herein.
Figure 9:
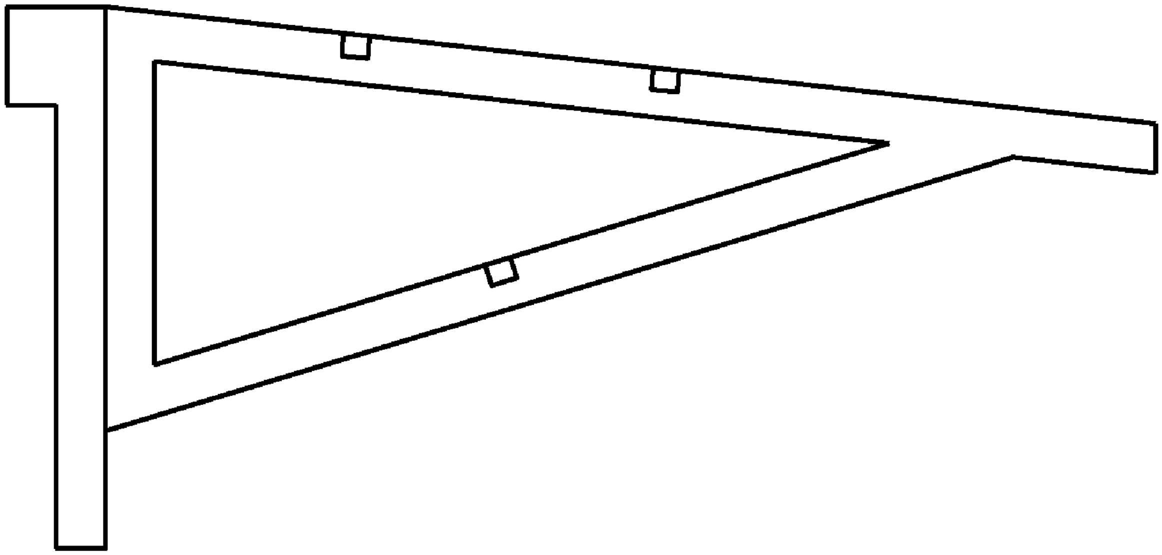
FIG. 9 is a side plan view of an eyewear device, according to an embodiment of the technology described herein.
Figure 10:
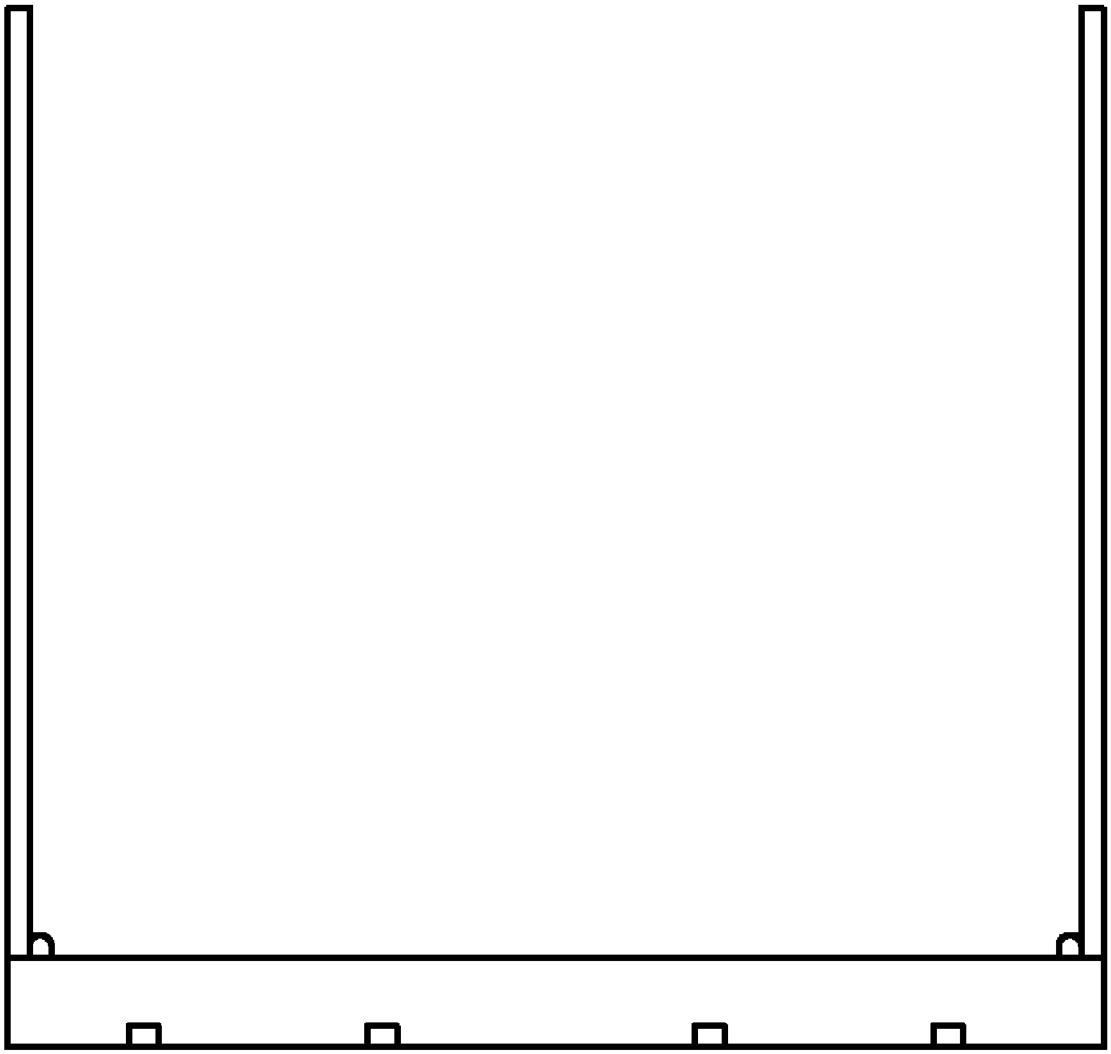
FIG. 10 is a top plan view of an eyewear device, according to an embodiment of the technology described herein.
Figure 11:
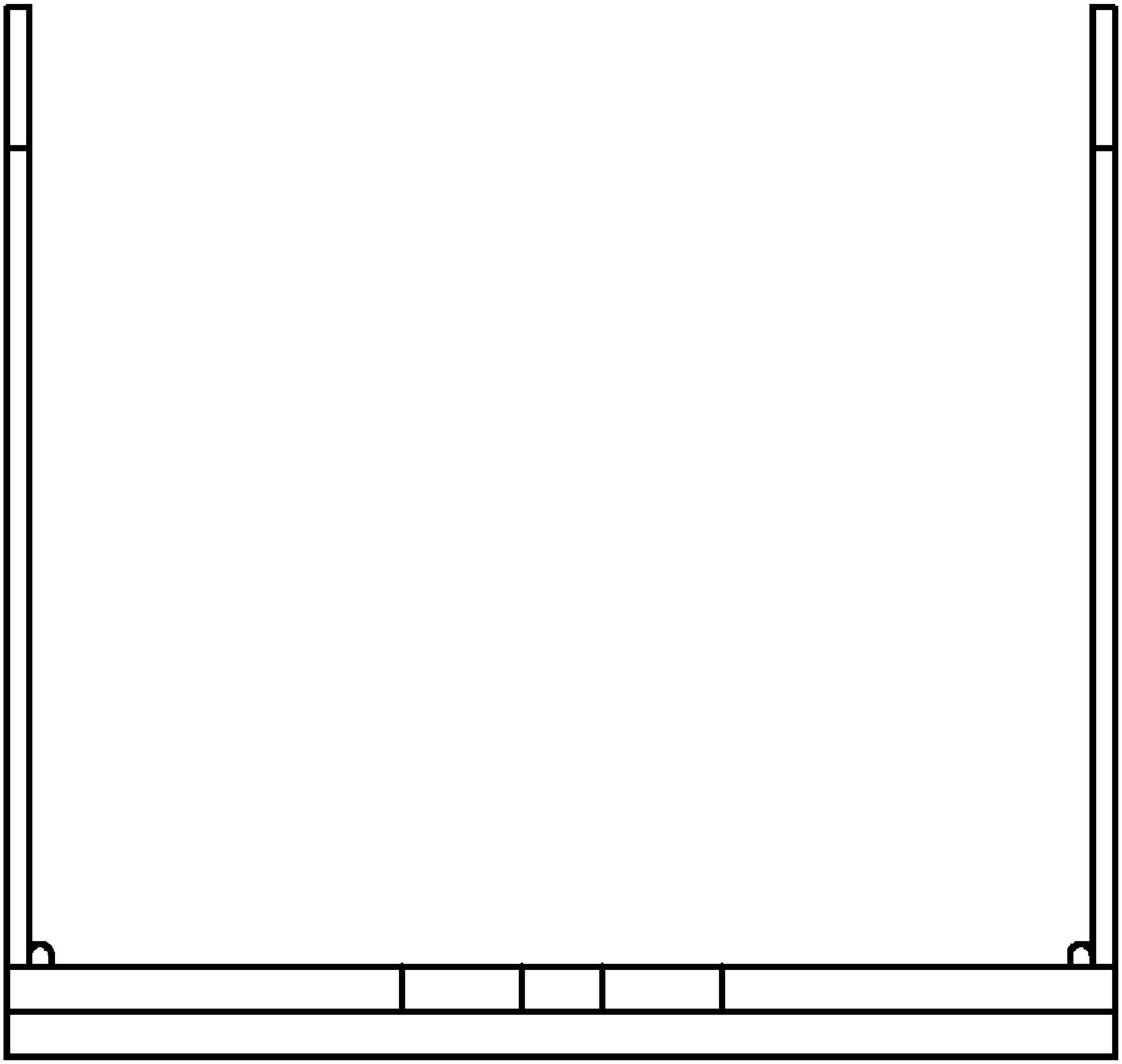
FIG. 11 is a bottom plan view of an eyewear device, according to an embodiment of the technology described herein.
Figure 12:
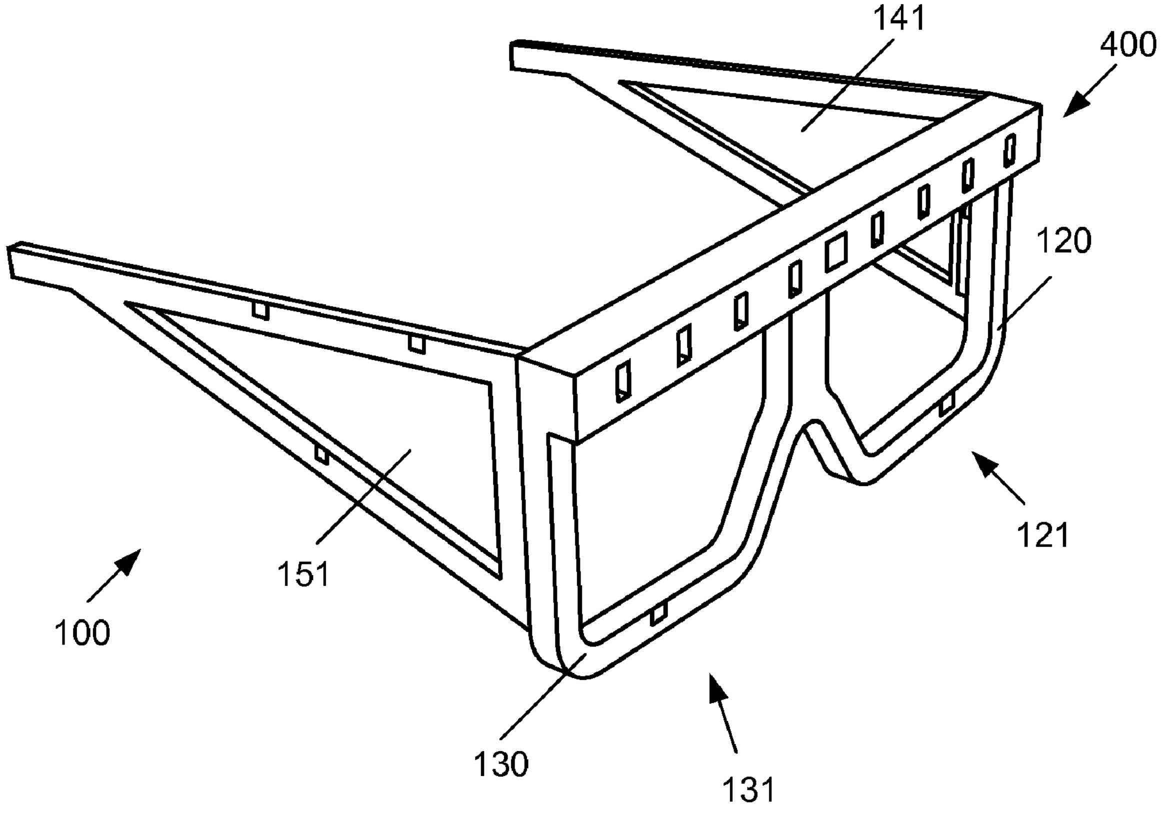
FIG. 12 is a perspective view of an eyewear device, according to an embodiment of the technology described herein.
Figure 13:
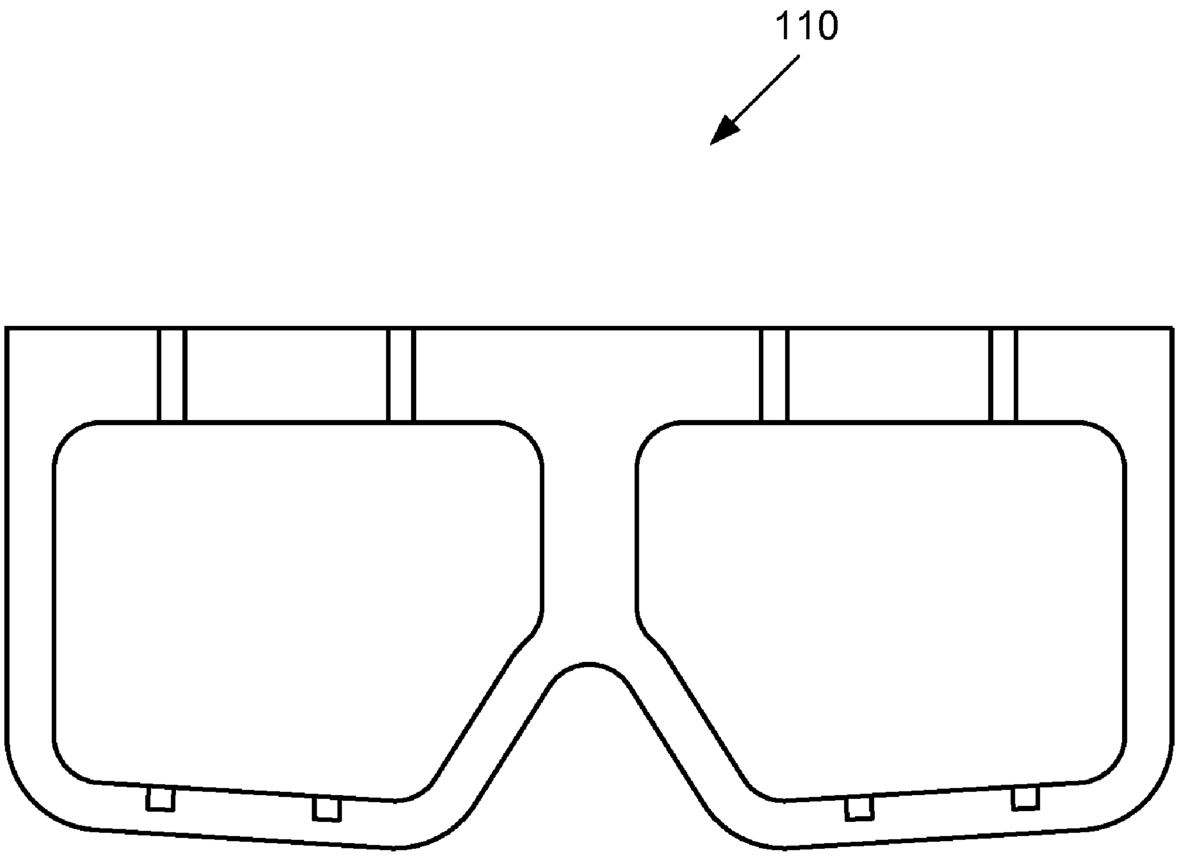
FIG. 13 is a front plan view of an eyewear device, illustrating, in particular, slots for inserting lenses, according to an embodiment of the technology described herein.
Figure 14:
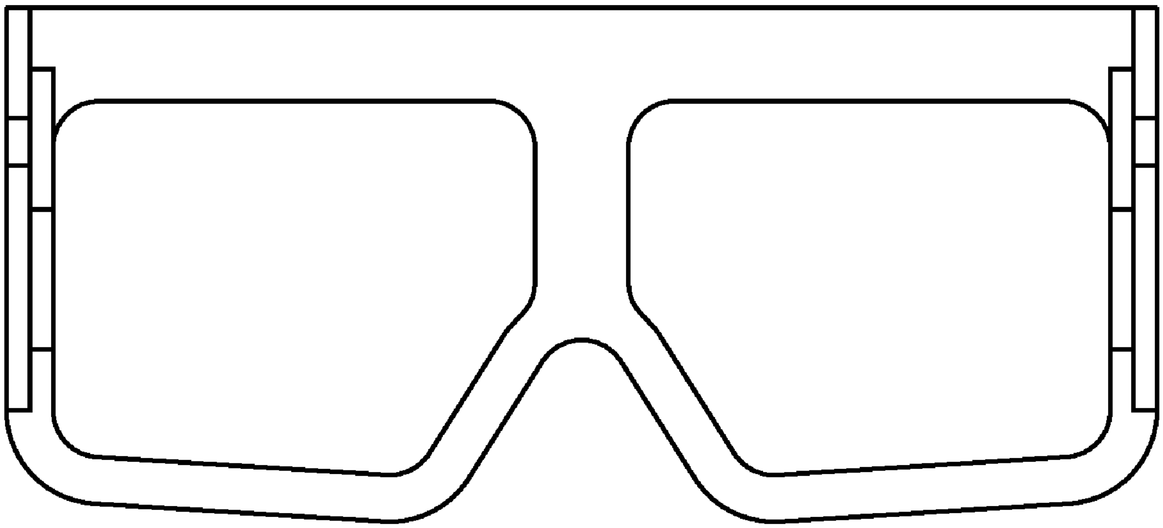
FIG. 14 is a rear plan view of the eyewear device of FIG. 13, according to an embodiment of the technology described herein.
Figure 15:
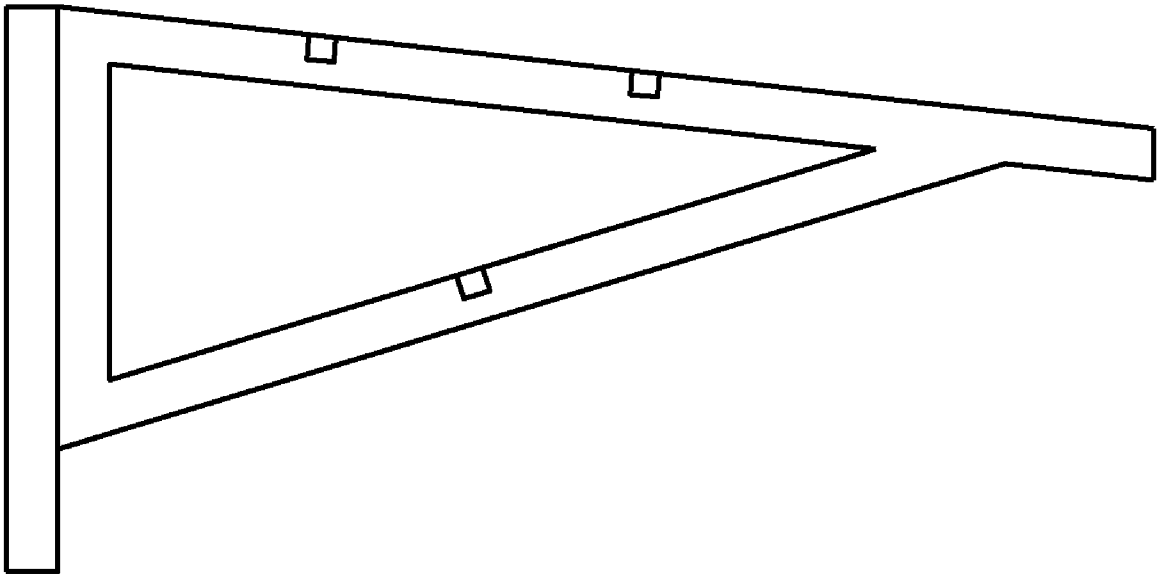
FIG. 15 is a side plan view of the eyewear device of FIG. 13, illustrating, in particular, slots for inserting lenses, according to an embodiment of the technology described herein.
Figure 16:
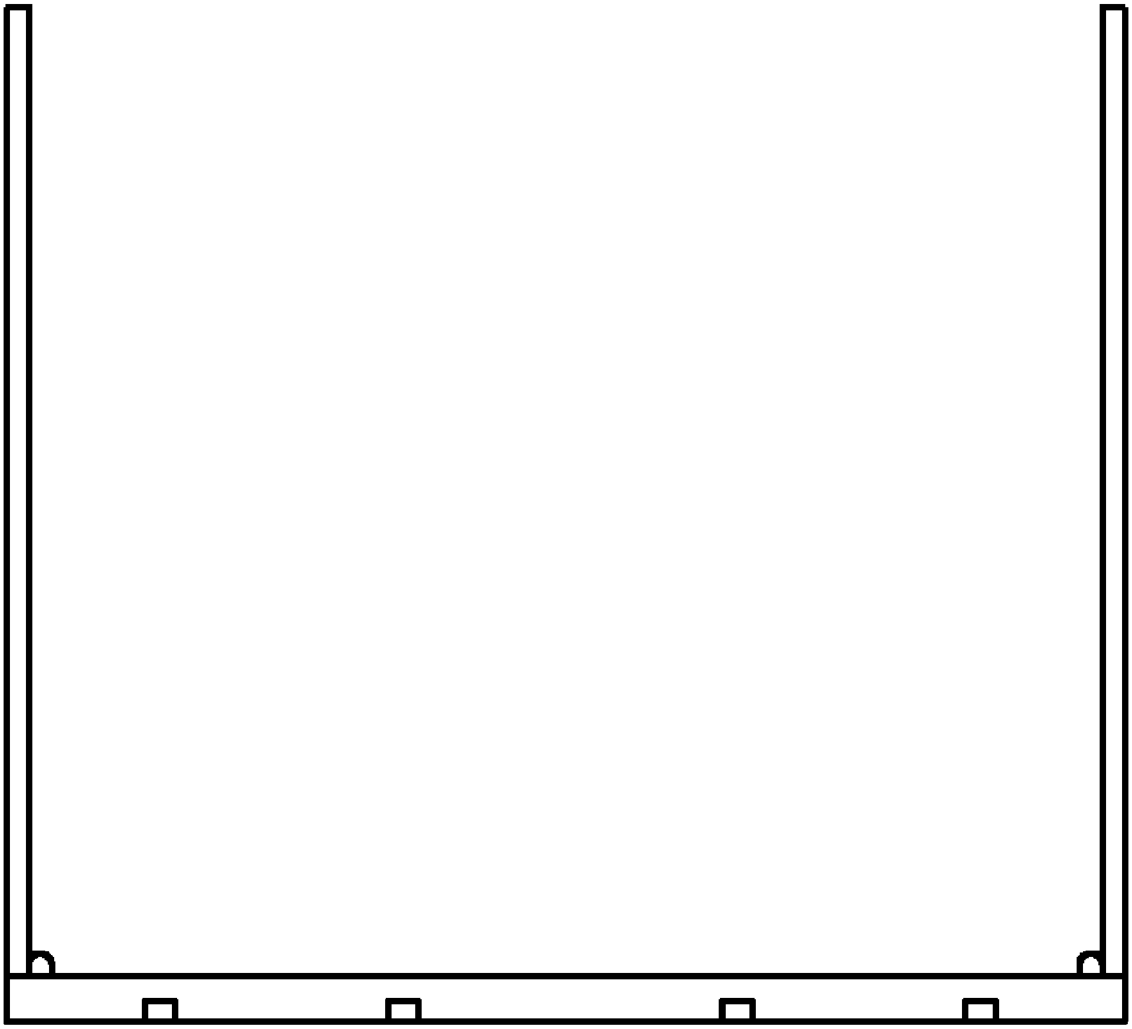
FIG. 16 is a top plan view of the eyewear device of FIG. 13, illustrating, in particular, slots for inserting lenses, according to an embodiment of the technology described herein.
Figure 17:
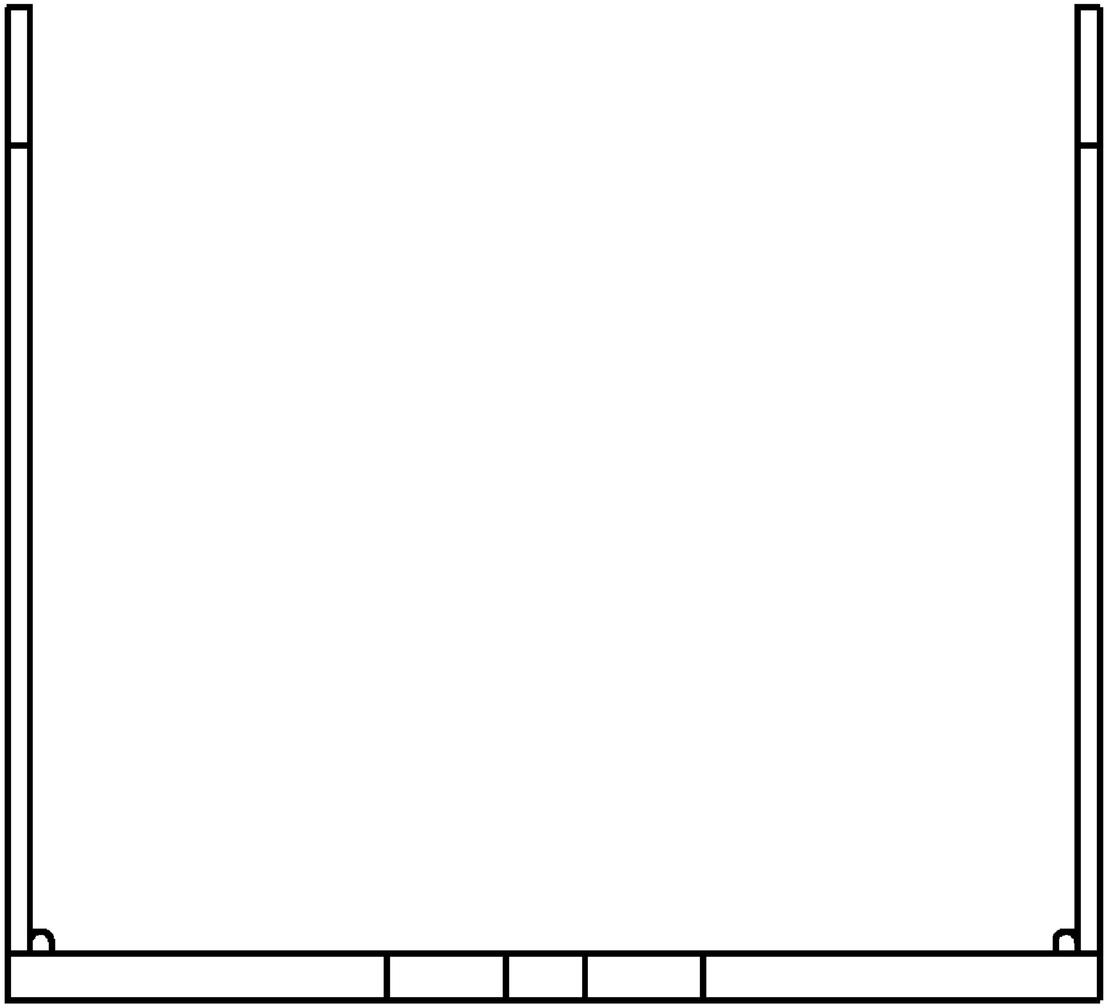
FIG. 17 is a bottom plan view of the eyewear device of FIG. 13, according to an embodiment of the technology described herein.
Figure 18:
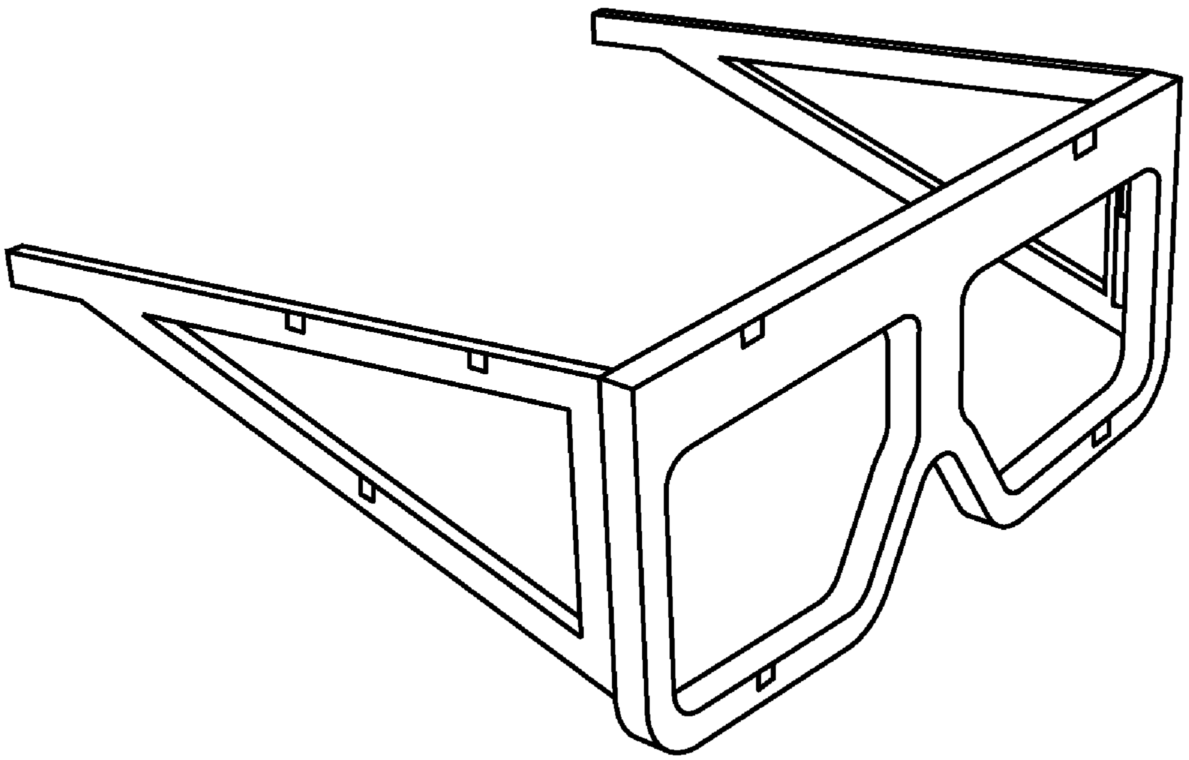
FIG. 18 is a perspective view of an eyewear device, illustrating, in particular, a slot arrangement for lens insertion, according to an embodiment of the technology described herein.
Figure 19:
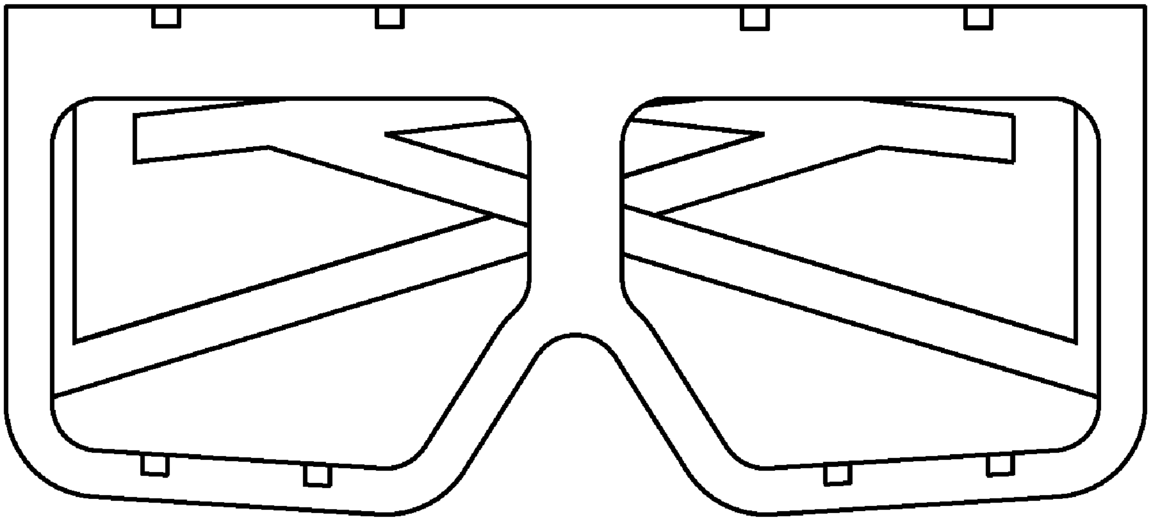
FIG. 19 is a front plan view of an eyewear device, illustrating, in particular, a slot arrangement for lens insertion, according to an embodiment of the technology described herein.
Figure 20:
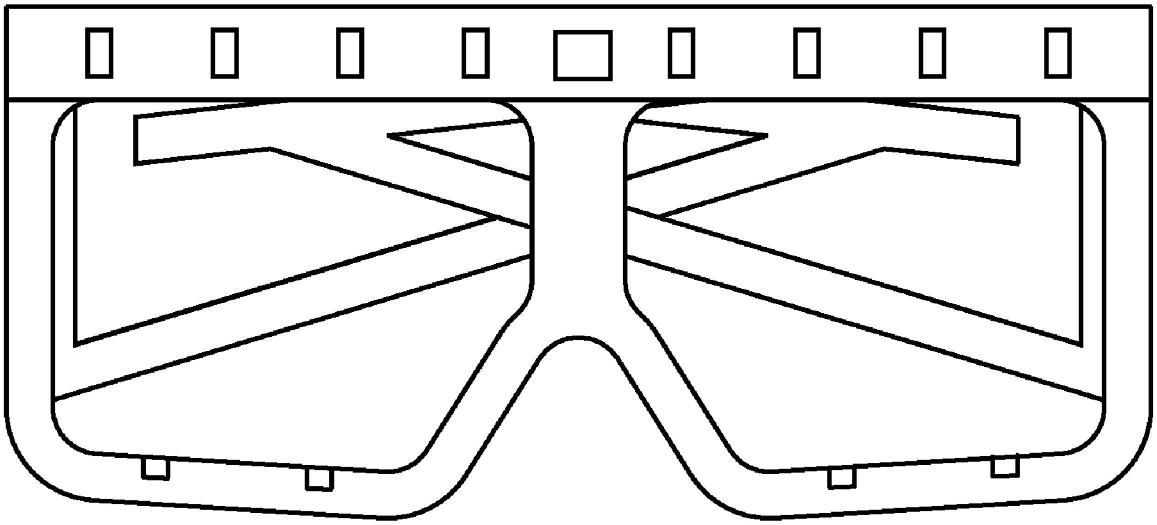
FIG. 20 is a front plan view of an eyewear device, illustrating, in particular, a slot arrangement for lens insertion, according to an embodiment of the technology described herein.
Figure 21:
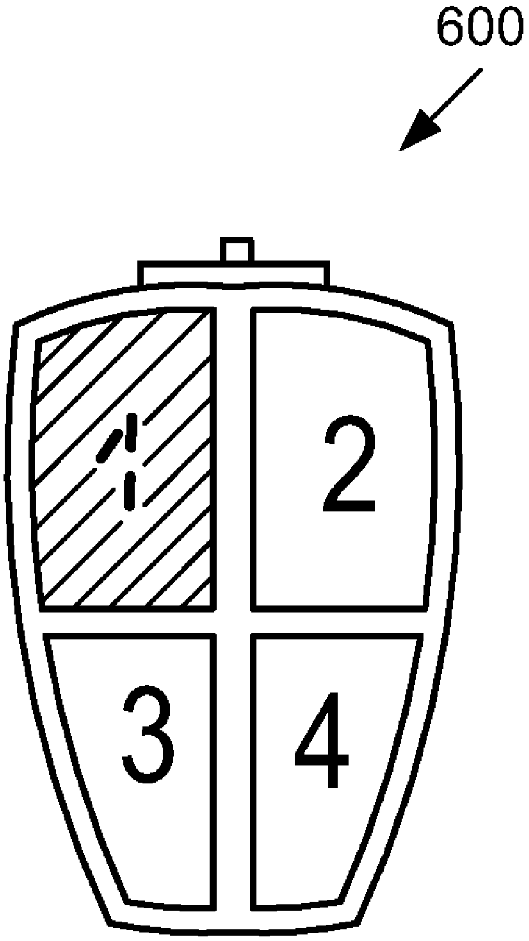
FIG. 21 is a front plan view of a button arrangement for a remote control device, illustrating, in particular, a film overlay on the desired button for home treatment, according to an embodiment of the technology described herein.
Figure 22A:
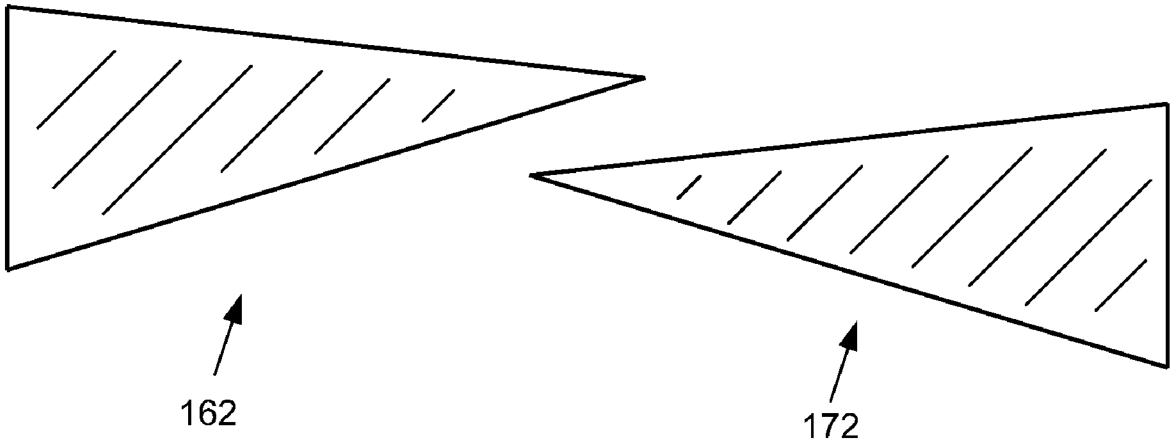
FIG. 22A is a front plan view of a pair of side lenses, illustrating, in particular, thin film occluded lenses for overlaying clear side lenses of an eyewear device, according to an embodiment of the technology described herein.
Figure 22B:
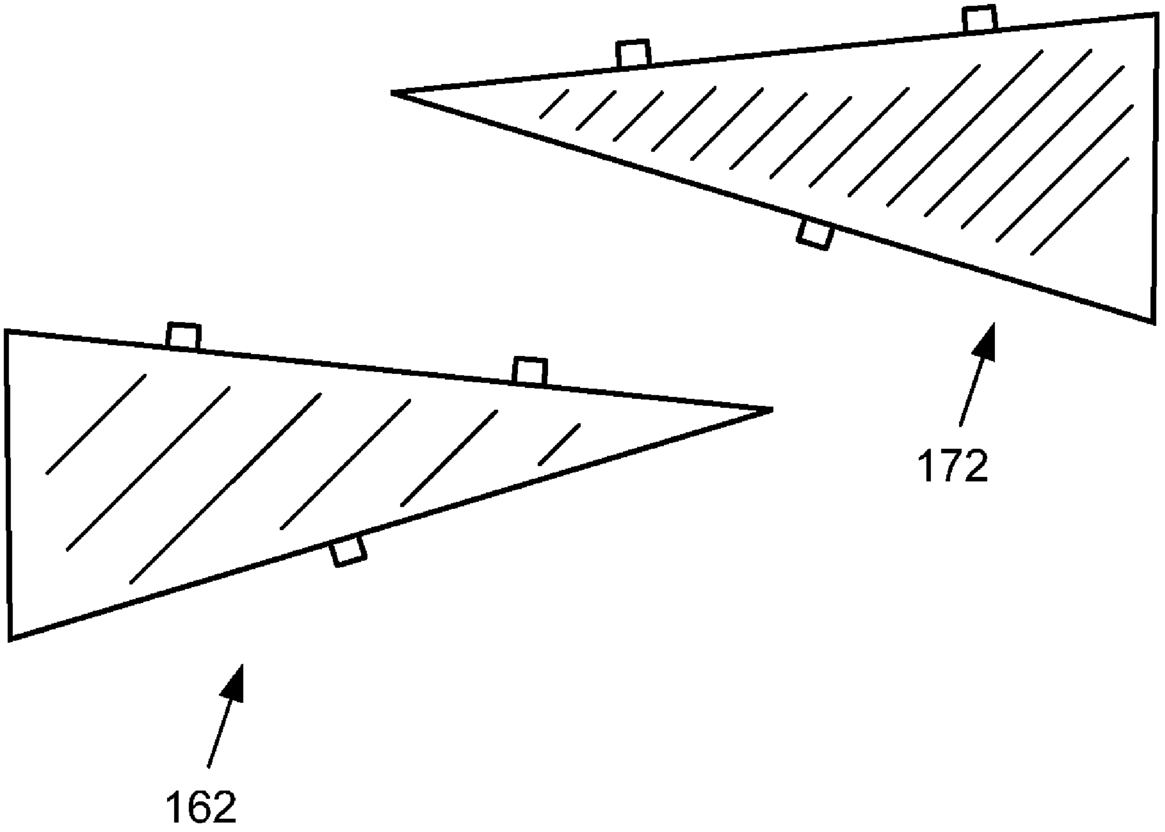
FIG. 22B is a front plan view of a pair of side lenses, illustrating, in particular, plastic occluded lenses for insertion into an eyewear device, according to an embodiment of the technology described herein.
Figure 23A:
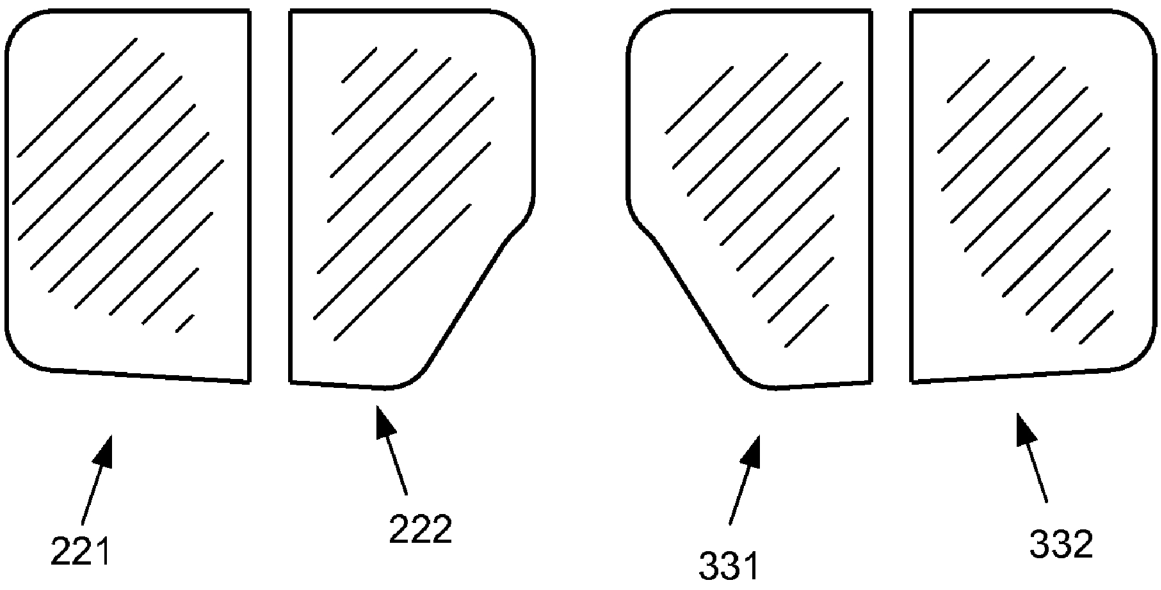
FIG. 23A is a front plan view of a pair of front lenses, illustrating, in particular, thin film occluded lenses for overlaying clear front lenses of an eyewear device, according to an embodiment of the technology described herein.
Figure 23B:
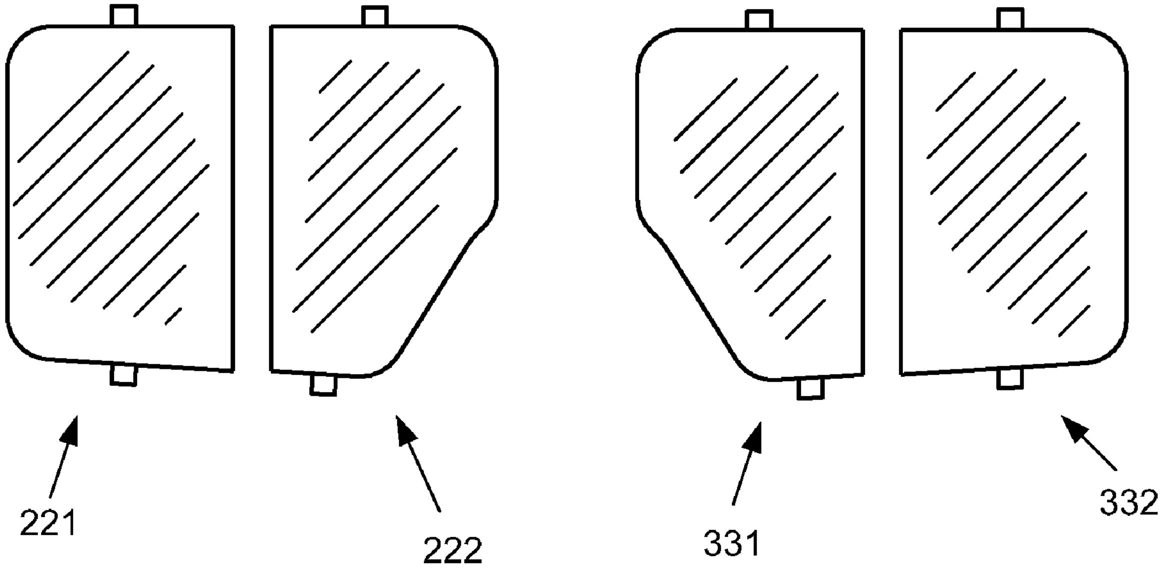
FIG. 23B is a front plan view of a pair of front lenses, illustrating, in particular, plastic occluded lenses for insertion into an eyewear device, according to an embodiment of the technology described herein.
Figure 24:
FIG. 24 is a front plan view of representative flash cards for use with an eyewear system, according to an embodiment of the technology described herein.
Figure 25:
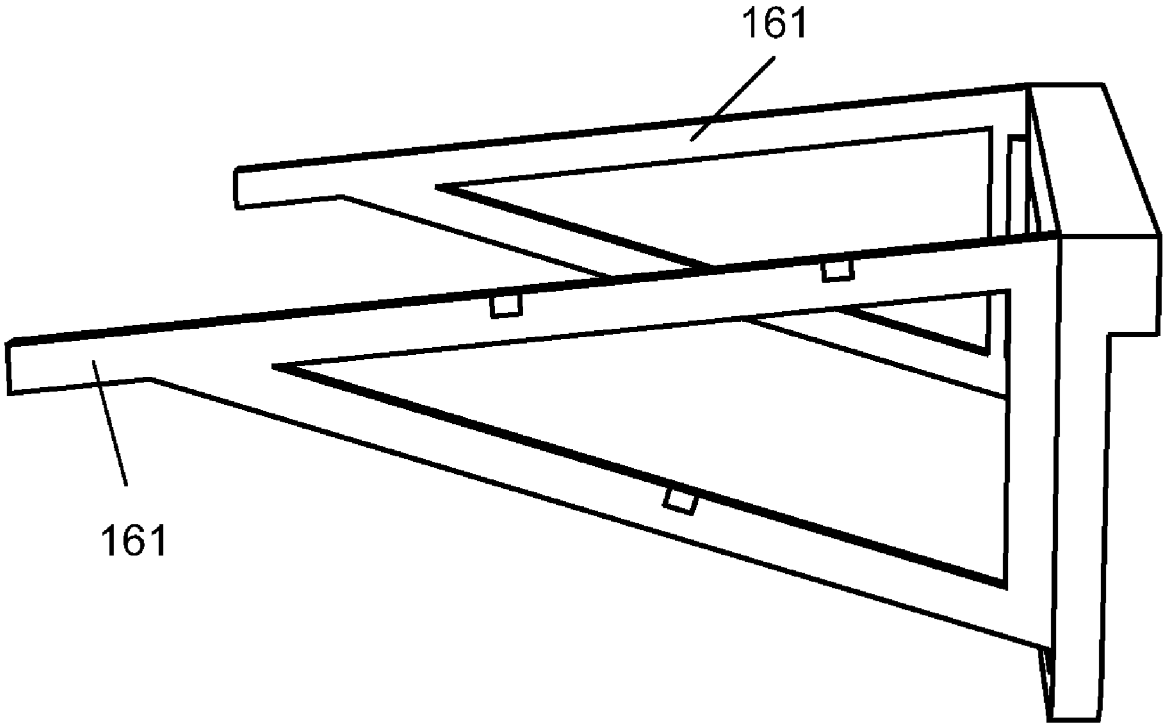
FIG. 25 is a side elevation view of an eyewear device, illustrating, in particular, the eyewear system device prior to insertion of side lenses, according to an embodiment of the technology described herein.
Figure 26:
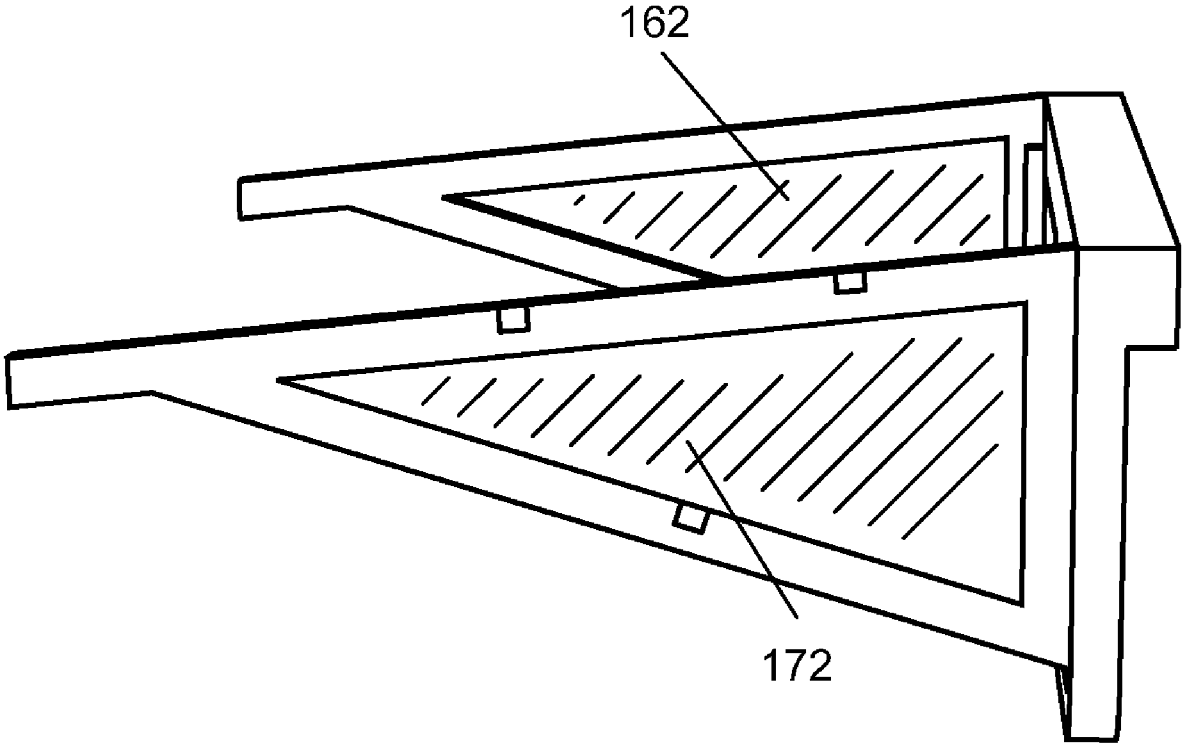
FIG. 26 is a side elevation view of an eyewear device, illustrating, in particular, the eyewear system device after insertion of side lenses, according to an embodiment of the technology described herein.

Referring now to FIGS. 1-26, an eyewear device 100 is shown, comprised of eyewear frames 110 having a left rim 120, a left lens area 121, a right rim 130 having a right lens area 131, a left side lens area 141 and a right side lens area 151.

In one embodiment of the technology described herein eyewear frames 110 for the treatment of unilateral neglect syndrome experienced by a subject comprises a left rim 120 having a left lens area 121 for receiving a first left lens 221 and a second left lens 222, the first and second left lenses configured for placement in the left lens area 121 individually or in combination, adjacent one to another; a right rim 130 having a right lens area 131 for receiving a first right lens 331 and a second right lens 332, the first and second right lenses configured for placement in the right lens area 131 individually or in combination, adjacent one to another; and wherein the eyewear frames 110 are configured for disposition upon a subject, and a left eye and a right eye are partially or fully occluded in a plurality of varied patterns, to aid in the treatment of unilateral neglect syndrome and stimulate response in a neglected side of the body of the subject.

In one embodiment of the technology described herein eyewear frames 110 for the treatment of unilateral neglect syndrome experienced by a subject comprise: a left rim 120 having a left lens area 121 for receiving a first and a second left lens, the first and second left lenses configured for placement in the left lens area 121 individually or in combination, adjacent one to another; a right rim 130 having a right lens area 131 for receiving a first and a second right lens, the first and second right lenses configured for placement in the right lens area 131 individually or in combination, adjacent one to another; a left end piece 161 hingedly attached to the left rim 120 and having a left temple area; a right end piece 171 hingedly attached to the right rim 130 and having a right temple area; a removable left temple block 162, configured for placement within the left temple area; and a removable right temple block 172, configured for placement within the right temple area; and where the eyewear frames 110 are configured for disposition upon a subject, and a left eye and a right eye are partially or fully occluded in a plurality of varied patterns, to aid in the treatment of unilateral neglect syndrome and stimulate response in a neglected side of the body of the subject.

In one embodiment of the technology described herein eyewear frames 110 for the treatment of unilateral neglect syndrome experienced by a subject comprise: a left rim 120 having a left lens area 121 for receiving a first and a second left lens, the first and second left lenses configured for placement in the left lens area 121 individually or in combination, adjacent one to another; a right rim 130 having a right lens area 131 for receiving a first and a second right lens, the first and second right lenses configured for placement in the right lens area 131 individually or in combination, adjacent one to another; a plurality of light-emitting diodes 400 (LEDs) disposed upon the eyewear frames 110 on an inside of the left and right rims and configured to emit a plurality of varied light patterns toward the subject to provide stimulation, a sensor 700 disposed upon the eyewear frames 110 and configured to activate the light-emitting diodes 400; and where the eyewear frames 110 are configured for disposition upon a subject, and a left eye and a right eye are partially or fully occluded in a plurality of varied patterns, to aid in the treatment of unilateral neglect syndrome and stimulate response in a neglected side of the body of the subject.

In one embodiment of the technology described herein eyewear frames 110 for the treatment of unilateral neglect syndrome experienced by a subject comprise: a left rim 120 having a left lens area 121 for receiving a first and a second left lens, the first and second left lenses configured for placement in the left lens area 121 individually or in combination, adjacent one to another; a right rim 130 having a right lens area 131 for receiving a first and a second right lens, the first and second right lenses configured for placement in the right lens area 131 individually or in combination, adjacent one to another; a plurality of light-emitting diodes 400 (LEDs) disposed upon the eyewear frames 110 on an inside of the left and right rims and configured to emit a plurality of varied light patterns toward the subject to provide stimulation; and where the eyewear frames 110 are configured for disposition upon a subject, and a left eye and a right eye are partially or fully occluded in a plurality of varied patterns, to aid in the treatment of unilateral neglect syndrome and stimulate response in a neglected side of the body of the subject, and where the plurality LEDs disposed upon the eyewear frames 110 on an inside of the left and right rims are further configured to operate in pairs, thereby able to illuminate two LEDs simultaneously, one LED proximate to the left eye, and another LED proximate to the right eye, thereby operative in tandem to draw the left and right eyes to scan and track toward a target direction.

In one embodiment of the technology described herein an eyewear system for the treatment of unilateral neglect syndrome experienced by a subject comprises: a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, a left end piece 161 hingedly attached to the left rim 120 and having a left temple area, a right end piece 171 hingedly attached to the right rim 130 and having a right temple area, a removable left temple block 162, configured for placement within the left temple area, and a removable right temple block 172, configured for placement within the right temple area; a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; where the first and second pairs of eyewear frames 110 are configured for interchangeable disposition upon a subject, and a left eye and a right eye are partially or fully occluded in a plurality of varied patterns, to aid in the treatment of unilateral neglect syndrome and stimulate response in a neglected side of the body of the subject.

In one embodiment of the technology described herein an eyewear system for the treatment of unilateral neglect syndrome experienced by a subject comprises: a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, a left end piece 161 hingedly attached to the left rim 120 and having a left temple area, a right end piece 171 hingedly attached to the right rim 130 and having a right temple area, a removable left temple block 162, configured for placement within the left temple area, and a removable right temple block 172, configured for placement within the right temple area; a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; a wireless remote control 600 configured for wireless connectivity to the plurality of LEDs disposed upon the second pair of eyewear frames 110 and configured to variably light the LEDs to provide varied stimulation to the eyes of the subject; and where the first and second pairs of eyewear frames 110 are configured for interchangeable disposition upon a subject, and a left eye and a right eye are partially or fully occluded in a plurality of varied patterns, to aid in the treatment of unilateral neglect syndrome and stimulate response in a neglected side of the body of the subject.

In one embodiment of the technology described herein an eyewear system for the treatment of unilateral neglect syndrome experienced by a subject comprises: a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, a left end piece 161 hingedly attached to the left rim 120 and having a left temple area, a right end piece 171 hingedly attached to the right rim 130 and having a right temple area, a removable left temple block 162, configured for placement within the left temple area, and a removable right temple block 172, configured for placement within the right temple area; a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; a wireless remote control 600 configured for wireless connectivity to the plurality of LEDs disposed upon the second pair of eyewear frames 110 and configured to variably light the LEDs to provide varied stimulation to the eyes of the subject; and where the first and second pairs of eyewear frames 110 are configured for interchangeable disposition upon a subject, and a left eye and a right eye are partially or fully occluded in a plurality of varied patterns, to aid in the treatment of unilateral neglect syndrome and stimulate response in a neglected side of the body of the subject, and where the wireless remote control 600 is configured with a number of buttons that is half the number of the plurality of LEDs disposed upon the second pair eyewear frames 110, and wherein each button is configured to, upon depression of the button, to illuminate two LEDs, one proximate to the left eye and another proximate to the right eye, thereby operative in tandem to draw the left and right eyes to scan and track toward a target direction.

In one embodiment of the technology described herein an eyewear system for the treatment of unilateral neglect syndrome experienced by a subject comprises: a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, a left end piece 161 hingedly attached to the left rim 120 and having a left temple area, a right end piece 171 hingedly attached to the right rim 130 and having a right temple area, a removable left temple block 162, configured for placement within the left temple area, and a removable right temple block 172, configured for placement within the right temple area; a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; a wireless remote control 600 configured for wireless connectivity to the plurality of LEDs disposed upon the second pair of eyewear frames 110 and configured to variably light the LEDs to provide varied stimulation to the eyes of the subject; a plurality of flashcards 500, each flashcard 500 having a unique thematic, illustrated diagram, the plurality of flashcards 500 configured for display one-at-a-time to the subject to obtain a plurality of test data and measure progress of the treatment for unilateral neglect syndrome; and where the first and second pairs of eyewear frames 110 are configured for interchangeable disposition upon a subject, and a left eye and a right eye are partially or fully occluded in a plurality of varied patterns, to aid in the treatment of unilateral neglect syndrome and stimulate response in a neglected side of the body of the subject.

In yet another embodiment of the technology described herein a method for treating unilateral neglect syndrome experienced by a subject comprises: utilizing a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, and wherein the eyewear frames 110 are configured for disposition upon a subject, and a left eye and a right eye are partially or fully occluded in a plurality of varied patterns, to aid in the treatment of unilateral neglect syndrome; and directing the subject to wear the first pair of eyewear frames 110 upon diagnosis of a cerebral vascular accident by a medical professional, and wherein the left lens area 121 for receiving a first and a second left lens and the right lens area 131 for receiving a first and a second right lens are partially occluded on a side of each eye corresponding to the side of the subject that is not suffering unilateral neglect.

In yet another embodiment of the technology described herein a method for treating unilateral neglect syndrome experienced by a subject comprises utilizing a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, and where the eyewear frames 110 are configured for disposition upon a subject, and a left eye and a right eye are partially or fully occluded in a plurality of varied patterns, to aid in the treatment of unilateral neglect syndrome; directing the subject to wear the first pair of eyewear frames 110 upon diagnosis of a cerebral vascular accident by a medical professional, and where the left lens area 121 for receiving a first and a second left lens and the right lens area 131 for receiving a first and a second right lens are partially occluded on a side of each eye corresponding to the side of the subject that is not suffering unilateral neglect, and where the first pair of eyewear frames 110 further comprises a left end piece 161 hingedly attached to the left rim 120 and having a left temple area; a right end piece 171 hingedly attached to the right rim 130 and having a right temple area; a removable left temple block 162, configured for placement within the left temple area; and a removable right temple block 172, configured for placement within the right temple area.

In yet another embodiment of the technology described herein a method for treating unilateral neglect syndrome experienced by a subject comprises utilizing a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, and wherein the eyewear frames 110 are configured for disposition upon a subject, and a left eye and a right eye are partially or fully occluded in a plurality of varied patterns, to aid in the treatment of unilateral neglect syndrome; directing the subject to wear the first pair of eyewear frames 110 upon diagnosis of a cerebral vascular accident by a medical professional; and utilizing a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; and interchangeably wearing the first and second pairs of eyewear frames 110 to aid in the treatment of unilateral neglect syndrome and stimulate response in a neglected side of the body of the subject, and where the left lens area 121 for receiving a first and a second left lens and the right lens area 131 for receiving a first and a second right lens are partially occluded on a side of each eye corresponding to the side of the subject that is not suffering unilateral neglect.

In yet another embodiment of the technology described herein a method for treating unilateral neglect syndrome experienced by a subject comprises: utilizing a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, and wherein the eyewear frames 110 are configured for disposition upon a subject, and a left eye and a right eye are partially or fully occluded in a plurality of varied patterns, to aid in the treatment of unilateral neglect syndrome; directing the subject to wear the first pair of eyewear frames 110 upon diagnosis of a cerebral vascular accident by a medical professional; and utilizing a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; and interchangeably wearing the first and second pairs of eyewear frames 110 to aid in the treatment of unilateral neglect syndrome and stimulate response in a neglected side of the body of the subject, and where the left lens area 121 for receiving a first and a second left lens and the right lens area 131 for receiving a first and a second right lens are partially occluded on a side of each eye corresponding to the side of the subject that is not suffering unilateral neglect, and where the second pair of eyewear frames 110 further comprises a left end piece 161 hingedly attached to the left rim 120 and having a left temple area; a right end piece 171 hingedly attached to the right rim 130 and having a right temple area; a removable left temple block 162, configured for placement within the left temple area; and a removable right temple block 172, configured for placement within the right temple area.

In yet another embodiment of the technology described herein a method for treating unilateral neglect syndrome experienced by a subject comprises: utilizing a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area

131 individually or in combination, adjacent one to another, and wherein the eyewear frames 110 are configured for disposition upon a subject, and a left eye and a right eye are partially or fully occluded in a plurality of varied patterns, to aid in the treatment of unilateral neglect syndrome; directing the subject to wear the first pair of eyewear frames 110 upon diagnosis of a cerebral vascular accident by a medical professional; utilizing a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; interchangeably wearing the first and second pairs of eyewear frames 110 to aid in the treatment of unilateral neglect syndrome and stimulate response in a neglected side of the body of the subject.

In yet another embodiment of the technology described herein a method for treating unilateral neglect syndrome experienced by a subject comprises: utilizing a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, and wherein the eyewear frames 110 are configured for disposition upon a subject, and a left eye and a right eye are partially or fully occluded in a plurality of varied patterns, to aid in the treatment of unilateral neglect syndrome; directing the subject to wear the first pair of eyewear frames 110 upon diagnosis of a cerebral vascular accident by a medical professional; utilizing a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; and interchangeably wearing the first and second pairs of eyewear frames 110 to aid in the treatment of unilateral neglect syndrome and stimulate response in a neglected side of the body of the subject; and where the second pair of eyewear frames 110 is further comprised of a left end piece 161 hingedly attached to the left rim 120 and having a left temple area; a right end piece 171 hingedly attached to the right rim 130 and having a right temple area; a removable left temple block 162, configured for placement within the left temple area; and a removable right temple block 172, configured for placement within the right temple area.

In yet another embodiment of the technology described herein a method for treating unilateral neglect syndrome experienced by a subject comprises utilizing a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, and wherein the eyewear frames 110 are configured for disposition upon a subject, and a left eye and a right eye are partially or fully occluded in a plurality of varied patterns, to aid in the treatment of unilateral neglect syndrome; directing the subject to wear the first pair of eyewear frames 110 upon diagnosis of a cerebral vascular accident by a medical professional; utilizing a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; interchangeably wearing the first and second pairs of eyewear frames 110 to aid in the treatment of unilateral neglect syndrome and stimulate response in a neglected side of the body of the subject; and utilizing a wireless remote control 600 configured for wireless connectivity to the plurality of LEDs disposed upon the second pair of eyewear frames 110 and configured to variably light the LEDs to provide varied stimulation to the eyes of the subject; and selectively lighting two or more LEDs, one proximate to the left eye and another proximate to the right eye, to provide varied stimulation to the eyes of the subject to draw the left and right eyes to scan and track toward a target direction.

In yet another embodiment of the technology described herein a method for treating unilateral neglect syndrome experienced by a subject comprises: utilizing a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, and wherein the eyewear frames 110 are configured for disposition upon a subject, and a left eye and a right eye are partially or fully occluded in a plurality of varied patterns, to aid in the treatment of unilateral neglect syndrome; directing the subject to wear the first pair of eyewear frames 110 upon diagnosis of a cerebral vascular accident by a medical professional; utilizing a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; interchangeably wearing the first and second pairs of eyewear frames 110 to aid in the treatment of unilateral neglect syndrome and stimulate response in a neglected side of the body of the subject, wherein the wireless remote control 600 is configured with a number of buttons that is half the number of the plurality of LEDs disposed upon the second pair eyewear frames 110, and wherein each button is configured to, upon depression of the button, to illuminate two LEDs, one proximate to the left eye and another proximate to the right eye, thereby operative in tandem to draw the left and right eyes to scan and track toward a target direction.

In yet another embodiment of the technology described herein a method for treating unilateral neglect syndrome experienced by a subject comprises: utilizing a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, and wherein the eyewear frames 110 are configured for disposition upon a subject, and a left eye and a right eye are partially or fully occluded in a plurality of varied patterns, to aid in the treatment of unilateral neglect syndrome; directing the subject to wear the first pair of eyewear frames 110 upon diagnosis of a cerebral vascular accident by a medical professional; and utilizing a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; and interchangeably wearing the first and second pairs of eyewear frames 110 to aid in the treatment of unilateral neglect syndrome and stimulate response in a neglected side of the body of the subject, and where the left lens area 121 for receiving a first and a second left lens and the right lens area 131 for receiving a first and a second right lens are partially occluded on a side of each eye corresponding to the side of the subject that is not suffering unilateral neglect, wherein the wireless remote control 600 is configured with a number of buttons that is half the number of the plurality of LEDs disposed upon the second pair eyewear frames 110, and wherein each button is configured to, upon depression of the button, to illuminate two LEDs, one proximate to the left eye and another proximate to the right eye, thereby operative in tandem to draw the left and right eyes to scan and track toward a target direction; utilizing a plurality of flashcards 500, each flashcard 500 having a unique thematic, illustrated diagram, the plurality of flashcards 500 configured for display one-at-a-time to the subject to obtain a plurality of test data and measure progress of the treatment for unilateral neglect syndrome; and presenting, from the neglected side of the body of the subject, the plurality of flashcards 500 one-at-a-time to obtain a plurality of test data and measure progress of the treatment for unilateral neglect syndrome.

In yet another embodiment of the technology described herein a method for treating unilateral neglect syndrome experienced by a subject comprises utilizing a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, and wherein the eyewear frames 110 are configured for disposition upon a subject, and a left eye and a right eye are partially or fully occluded in a plurality of varied patterns, to aid in the treatment of unilateral neglect syndrome; directing the subject to wear the first pair of eyewear frames 110 upon diagnosis of a cerebral vascular accident by a medical professional; utilizing a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; interchangeably wearing the first and second pairs of eyewear frames 110 to aid in the treatment of unilateral neglect syndrome and stimulate response in a neglected side of the body of the subject; and utilizing a wireless remote control 600 configured for wireless connectivity to the plurality of LEDs disposed upon the second pair of eyewear frames 110 and configured to variably light the LEDs to provide varied stimulation to the eyes of the subject; and selectively lighting two or more LEDs, one proximate to the left eye and another proximate to the right eye, to provide varied stimulation to the eyes of the subject to draw the left and right eyes to scan and track toward a target direction; utilizing a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, and wherein the eyewear frames 110 are configured for disposition upon a subject, and a left eye and a right eye are partially or fully occluded in a plurality of varied patterns, to aid in the treatment of unilateral neglect syndrome; directing the subject to wear the first pair of eyewear frames 110 upon diagnosis of a cerebral vascular accident by a medical professional; and utilizing a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; and interchangeably wearing the first and second pairs of eyewear frames 110 to aid in the treatment of unilateral neglect syndrome and stimulate response in a neglected side of the body of the subject, and where the left lens area 121 for receiving a first and a second left lens and the right lens area 131 for receiving a first and a second right lens are partially occluded on a side of each eye corresponding to the side of the subject that is not suffering unilateral neglect, wherein the wireless remote control 600 is configured with a number of buttons that is half the number of the plurality of LEDs disposed upon the second pair eyewear frames 110, and wherein each button is configured to, upon depression of the button, to illuminate two LEDs, one proximate to the left eye and another proximate to the right eye, thereby operative in tandem to draw the left and right eyes to scan and track toward a target direction; placing the first and second left lenses in the left lens area 121 in combination; placing the first and second right lenses in the right lens area 131 in combination; placing the removable left temple block 162 in the left temple area; placing the removable right temple block 172 in the right temple area; and placing the second pair of eyewear frames 110 on the subject.

In yet another embodiment of the technology described herein a method for treating unilateral neglect syndrome experienced by a subject comprises: utilizing a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, and wherein the eyewear frames 110 are configured for disposition upon a subject, and a left eye and a right eye are partially or fully occluded in a plurality of varied patterns, to aid in the treatment of unilateral neglect syndrome; directing the subject to wear the first pair of eyewear frames 110 upon diagnosis of a cerebral vascular accident by a medical professional; and utilizing a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; and interchangeably wearing the first and second pairs of eyewear frames 110 to aid in the treatment of unilateral neglect syndrome and stimulate response in a neglected side of the body of the subject, and where the left lens area 121 for receiving a first and a second left lens and the right lens area 131 for receiving a first and a second right lens are partially occluded on a side of each eye corresponding to the side of the subject that is not suffering unilateral neglect, wherein the wireless remote control 600 is configured with a number of buttons that is half the number of the plurality of LEDs disposed upon the second pair eyewear frames 110, and wherein each button is configured to, upon depression of the button, to illuminate two LEDs, one proximate to the left eye and another proximate to the right eye, thereby operative in tandem to draw the left and right eyes to scan and track toward a target direction; selectively lighting, as the subject gains consistency in LED light recognition, two or more LEDs, one proximate to the left eye and another proximate to the right eye, the LEDs being further away from a current field of vision of the subject and closer to a neglected side of the body of the subject.

In yet another embodiment of the technology described herein a method for treating unilateral neglect syndrome experienced by a subject comprises: utilizing a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, and wherein the eyewear frames 110 are configured for disposition upon a subject, and a left eye and a right eye are partially or fully occluded in a plurality of varied patterns, to aid in the treatment of unilateral neglect syndrome; directing the subject to wear the first pair of eyewear frames 110 upon diagnosis of a cerebral vascular accident by a medical professional; and utilizing a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; and interchangeably wearing the first and second pairs of eyewear frames 110 to aid in the treatment of unilateral neglect syndrome and stimulate response in a neglected side of the body of the subject, and where the left lens area 121 for receiving a first and a second left lens and the right lens area 131 for receiving a first and a second right lens are partially occluded on a side of each eye corresponding to the side of the subject that is not suffering unilateral neglect, wherein the wireless remote control 600 is configured with a number of buttons that is half the number of the plurality of LEDs disposed upon the second pair eyewear frames 110, and wherein each button is configured to, upon depression of the button, to illuminate two LEDs, one proximate to the left eye and another proximate to the right eye, thereby operative in tandem to draw the left and right eyes to scan and track toward a target direction; utilizing a progression scale to observe and record the progression of the subject in the treatment of unilateral neglect syndrome, the progression scale comprising levels: severe, wherein the subject focuses on one side of the body and rarely tracks or scans past a midline; moderate, wherein the subject focuses on one side of the body, may track or scan past midline with constant verbal cueing, however quickly returns focus to the neglected side of the body; minimal, wherein the subject focuses on one side of the body, will track or scan with verbal cueing; and intermittent, wherein the subject focuses on one side of the body, does not require verbal cueing to track or scan past midline, however may not be able to recall one item viewed while looking to the neglected side; and assigning a level from the progression scale to the subject to note progression of the subject.

In yet another embodiment of the technology described herein a method for treating unilateral neglect syndrome experienced by a subject comprises: utilizing a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, and wherein the eyewear frames 110 are configured for disposition upon a subject, and a left eye and a right eye are partially or fully occluded in a plurality of varied patterns, to aid in the treatment of unilateral neglect syndrome; directing the subject to wear the first pair of eyewear frames 110 upon diagnosis of a cerebral vascular accident by a medical professional; and utilizing a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; and interchangeably wearing the first and second pairs of eyewear frames 110 to aid in the treatment of unilateral neglect syndrome and stimulate response in a neglected side of the body of the subject, and where the left lens area 121 for receiving a first and a second left lens and the right lens area 131 for receiving a first and a second right lens are partially occluded on a side of each eye corresponding to the side of the subject that is not suffering unilateral neglect, wherein the wireless remote control 600 is configured with a number of buttons that is half the number of the plurality of LEDs disposed upon the second pair eyewear frames 110, and wherein each button is configured to, upon depression of the button, to illuminate two LEDs, one proximate to the left eye and another proximate to the right eye, thereby operative in tandem to draw the left and right eyes to scan and track toward a target direction; utilizing a progression scale to observe and record the progression of the subject in the treatment of unilateral neglect syndrome, the progression scale comprising levels: severe, wherein the subject focuses on one side of the body and rarely tracks or scans past a midline; moderate, wherein the subject focuses on one side of the body, may track or scan past midline with constant verbal cueing, however quickly returns focus to the neglected side of the body; minimal, wherein the subject focuses on one side of the body, will track or scan with verbal cueing; and intermittent, wherein the subject focuses on one side of the body, does not require verbal cueing to track or scan past midline, however may not be able to recall one item viewed while looking to the neglected side; and assigning a level from the progression scale to the subject to note progression of the subject, wherein the plurality of LEDs is comprised of eight LEDs, four proximate to each eye, and linearly disposed upon the eyewear frames 110, and wherein the wireless remote control 600 is configured with four buttons, button one illuminating LEDs one and five, button two illuminating LEDs two and six, button one illuminating LEDs three and seven, and button four illuminating LEDs four and eight, the method further comprising: selectively operating the wireless remote control 600, in treating left side neglect, based upon the performance of the subject as observed on the progression scale: severe, utilizing button four until consistent recognition of LEDs is met; moderate, utilizing button three until consistent recognition of LEDs is met; minimal, utilizing button two until consistent recognition of LEDs is met; intermittent, utilizing button one until consistent recognition of LEDs is met; and selectively operating the wireless remote control 600, in treating right side neglect, based upon the performance of the subject as observed on the progression scale: severe, utilizing button one until consistent recognition of LEDs is met; moderate, utilizing button two until consistent recognition of LEDs is met; minimal, utilizing button three until consistent recognition of LEDs is met; intermittent, utilizing button four until consistent recognition of LEDs is met.

In yet another embodiment of the technology described herein a method for treating unilateral neglect syndrome experienced by a subject comprises: utilizing a first pair of eyewear frames 110 having a left rim 120 having a left lens area 121 for receiving a first and a second left lens, the first and second left lenses configured for placement in the left lens area 121 individually or in combination, adjacent one to another, a right rim 130 having a right lens area 131 for receiving a first and a second right lens, the first and second right lenses configured for placement in the right lens area 131 individually or in combination, adjacent one to another, and wherein the eyewear frames 110 are configured for disposition upon a subject, and a left eye and a right eye are partially or fully occluded in a plurality of varied patterns, to aid in the treatment of unilateral neglect syndrome; directing the subject to wear the first pair of eyewear frames 110 upon diagnosis of a cerebral vascular accident by a medical professional; and utilizing a second pair of eyewear frames 110 having all elements of the first pair of eyewear frames 110 and additionally having a plurality of light-emitting diodes 400 (LEDs) disposed upon the second pair eyewear frames 110 on an inside of the left and right rims and configured to emit a plurality of varied light patterns toward the subject to provide stimulation; and interchangeably wearing the first and second pairs of eyewear frames 110 to aid in the treatment of unilateral neglect syndrome and stimulate response in a neglected side of the body of the subject, and where the left lens area 121 for receiving a first and a second left lens and the right lens area 131 for receiving a first and a second right lens are partially occluded on a side of each eye corresponding to the side of the subject that is not suffering unilateral neglect, wherein the wireless remote control 600 is configured with a number of buttons that is half the number of the plurality of LEDs disposed upon the second pair eyewear frames 110, and wherein each button is configured to, upon depression of the button, to illuminate two LEDs, one proximate to the left eye and another proximate to the right eye, thereby operative in tandem to draw the left and right eyes to scan and track toward a target direction; utilizing a plurality of flashcards 500, each flashcard 500 having a unique thematic, illustrated diagram, the plurality of flashcards 500 configured for display one-at-a-time to the subject to obtain a plurality of test data and measure progress of the treatment for unilateral neglect syndrome; and presenting, from the neglected side of the body of the subject, the plurality of flashcards 500 one-at-a-time to obtain a plurality of test data and measure progress of the treatment for unilateral neglect syndrome; removing the second pair of eyewear frames 110 from the subject upon completion of the treatment session; and placing the first pair of eyewear frames 110 on the subject to facilitate visual retraining.

Although this technology has been illustrated and described herein with reference to preferred embodiments and specific examples thereof, it will be readily apparent to those of ordinary skill in the art that other embodiments and examples can perform similar functions and/or achieve like results. All such equivalent embodiments and examples are within the spirit and scope of the invention and are intended to be covered by the following claims.

What is claimed is:

1. An eyewear system for the treatment of unilateral neglect syndrome experienced by a subject, the system comprising:

a first pair of eyewear frames having a left rim having a left lens area for receiving a first and a second left lens, the first and second left lenses configured for placement in the left lens area individually or in combination, adjacent one to another, a right rim having a right lens area for receiving a first and a second right lens, the first and second right lenses configured for placement in the right lens area individually or in combination, adjacent one to another, a left end piece hingedly attached to the left rim and having a left temple area, a right end piece hingedly attached to the right rim and having a right temple area, a removable left temple block, configured for placement within the left temple area, and a removable right temple block, configured for placement within the right temple area;

a second pair of eyewear frames having all elements of the first pair of eyewear frames and additionally having a plurality of light-emitting diodes (LEDs) disposed upon the second pair eyewear frames on an inside of the left and right rims and configured to emit a plurality of varied light patterns toward the subject to provide stimulation; and wherein the first and second pairs of eyewear frames are configured for interchangeable disposition upon a subject, and a left eye and a right eye are partially or fully occluded in a plurality of varied patterns, to aid in the treatment of unilateral neglect syndrome and stimulate response in a neglected side of the body of the subject.

2. The eyewear system of claim 1, further comprising:

a remote control configured for wireless connectivity to the plurality of LEDs disposed upon the second pair of eyewear frames and configured to variably light the LEDs to provide varied stimulation to the eyes of the subject.

3. The eyewear system of claim 2, wherein the remote control is wireless and is configured with a number of buttons that is half the number of the plurality of LEDs disposed upon the second pair eyewear frames, and wherein each button is configured to, upon depression of the button, to illuminate two LEDs, one proximate to the left eye and another proximate to the right eye, thereby operative in tandem to draw the left and right eyes to scan and track toward a target direction.

4. The eyewear system of claim 2, further comprising:

a plurality of flashcards, each flashcard having a unique thematic, illustrated diagram, the plurality of flashcards configured for display one-at-a-time to the subject to obtain a plurality of test data and measure progress of the treatment for unilateral neglect syndrome.

5. A method for treating unilateral neglect syndrome experienced by a subject, the method comprising:

utilizing a first pair of eyewear frames having a left rim having a left lens area for receiving a first and a second left lens, the first and second left lenses configured for placement in the left lens area individually or in combination, adjacent one to another, a right rim having a right lens area for receiving a first and a second right lens, the first and second right lenses configured for placement in the right lens area individually or in combination, adjacent one to another, and wherein the eyewear frames are configured for disposition upon a subject, and a left eye and a right eye are partially or fully occluded in a plurality of varied patterns, to aid in the treatment of unilateral neglect syndrome; and directing the subject to wear the first pair of eyewear frames upon diagnosis of a cerebral vascular accident by a medical professional, and wherein the left lens area for receiving a first and a second left lens and the right lens area for receiving a first and a second right lens are partially occluded on a side of each eye corresponding to the side of the subject that is not suffering unilateral neglect.

6. The method of claim 5, wherein the first pair of eyewear frames further comprises:

a left end piece hingedly attached to the left rim and having a left temple area;

a right end piece hingedly attached to the right rim and having a right temple area;

a removable left temple block, configured for placement within the left temple area; and a removable right temple block, configured for placement within the right temple area.

7. The method of claim 5, further comprising:

utilizing a second pair of eyewear frames having all elements of the first pair of eyewear frames and additionally having a sensor operable connected to a plurality of light-emitting diodes (LEDs) disposed upon the second pair eyewear frames on an inside of the left and right rims and configured to emit a plurality of varied light patterns toward the subject to provide stimulation; and interchangeably wearing the first and second pairs of eyewear frames to aid in the treatment of unilateral neglect syndrome and stimulate response in a neglected side of the body of the subject.

8. The method of claim 7, wherein the second pair of eyewear frames further comprises:

a left end piece hingedly attached to the left rim and having a left temple area;

a right end piece hingedly attached to the right rim and having a right temple area;

a removable left temple block, configured for placement within the left temple area; and a removable right temple block, configured for placement within the right temple area.

9. The method of claim 7, further comprising:

utilizing a wireless remote control configured for wireless connectivity to the plurality of LEDs disposed upon the second pair of eyewear frames and configured to variably light the LEDs to provide varied stimulation to the eyes of the subject; and selectively lighting two or more LEDs, one proximate to the left eye and another proximate to the right eye, to provide varied stimulation to the eyes of the subject to draw the left and right eyes to scan and track toward a target direction.

10. The method of claim 9, further comprising:

utilizing a plurality of flashcards, each flashcard having a unique thematic, illustrated diagram, the plurality of flashcards configured for display one-at-a-time to the subject to obtain a plurality of test data and measure progress of the treatment for unilateral neglect syndrome; and presenting, from the neglected side of the body of the subject, the plurality of flashcards one-at-a-time to obtain a plurality of test data and measure progress of the treatment for unilateral neglect syndrome.

11. The method of claim 10, further comprising:

removing the second pair of eyewear frames from the subject upon completion of the treatment session; and placing the first pair of eyewear frames on the subject to facilitate visual retraining.

12. The method of claim 9, further comprising:

placing the first and second left lenses in the left lens area in combination;

placing the first and second right lenses in the right lens area in combination;

placing the removable left temple block in the left temple area;

placing the removable right temple block in the right temple area; and placing the second pair of eyewear frames on the subject.

13. The method of claim 9, further comprising:

selectively lighting, as the subject gains consistency in LED light recognition, two or more LEDs, one proximate to the left eye and another proximate to the right eye, the LEDs being further away from a current field of vision of the subject and closer to a neglected side of the body of the subject.

14. The method of claim 9, further comprising:

utilizing a progression scale to observe and record the progression of the subject in the treatment of unilateral neglect syndrome, the progression scale comprising levels:

severe, wherein the subject focuses on one side of the body and rarely tracks or scans past a midline;

moderate, wherein the subject focuses on one side of the body, may track or scan past midline with constant verbal cueing, however quickly returns focus to the neglected side of the body;

minimal, wherein the subject focuses on one side of the body, will track or scan with verbal cueing; and intermittent, wherein the subject focuses on one side of the body, does not require verbal cueing to track or scan past midline, however may not be able to recall one item viewed while looking to the neglected side; and assigning a level from the progression scale to the subject to note progression of the subject.

15. The method of claim 14, wherein the plurality of LEDs is comprised of eight LEDs, four proximate to each eye, and linearly disposed upon the eyewear frames, and wherein the wireless remote control is configured with four buttons, button one illuminating LEDs one and five, button two illuminating LEDs two and six, button one illuminating LEDs three and seven, and button four illuminating LEDs four and eight, the method further comprising:

selectively operating the wireless remote control, in treating left side neglect, based upon the performance of the subject as observed on the progression scale:

severe, utilizing button four until consistent recognition of LEDs is met;

moderate, utilizing button three until consistent recognition of LEDs is met;

minimal, utilizing button two until consistent recognition of LEDs is met;

intermittent, utilizing button one until consistent recognition of LEDs is met; and selectively operating the wireless remote control, in treating right side neglect, based upon the performance of the subject as observed on the progression scale:

severe, utilizing button one until consistent recognition of LEDs is met;

moderate, utilizing button two until consistent recognition of LEDs is met;

minimal, utilizing button three until consistent recognition of LEDs is met;

intermittent, utilizing button four until consistent recognition of LEDs is met.

16. The method of claim 7, wherein the wireless remote control is configured with a number of buttons that is half the number of the plurality of LEDs disposed upon the second pair eyewear frames, and wherein each button is configured to, upon depression of the button, to illuminate two LEDs, one proximate to the left eye and another proximate to the right eye, thereby operative in tandem to draw the left and right eyes to scan and track toward a target direction.

* * * * *